(12) United States Patent
Truckai et al.

(10) Patent No.: US 6,656,177 B2
(45) Date of Patent: *Dec. 2, 2003

(54) ELECTROSURGICAL SYSTEMS AND TECHNIQUES FOR SEALING TISSUE

(76) Inventors: Csaba Truckai, 19566 Arden Ct., Saratoga, CA (US) 95070; John H. Shadduck, 1490 Vistazo West, Tiburon, CA (US) 94920

(*) Notice: Subject to any disclaimer, the term of this patent is extended or adjusted under 35 U.S.C. 154(b) by 0 days.

This patent is subject to a terminal disclaimer.

(21) Appl. No.: 10/079,728

(22) Filed: Feb. 19, 2002

(65) Prior Publication Data

US 2002/0115997 A1 Aug. 22, 2002

Related U.S. Application Data

(63) Continuation-in-part of application No. 09/694,233, filed on Oct. 23, 2000.
(60) Provisional application No. 60/270,982, filed on Feb. 23, 2001.

(51) Int. Cl.[7] .............................................. A61B 18/18
(52) U.S. Cl. ........................... 606/51; 606/52; 606/210; 606/205
(58) Field of Search ...................................... 606/32–52

(56) References Cited

U.S. PATENT DOCUMENTS

| | | | | |
|---|---|---|---|---|
| 5,190,541 A | * | 3/1993 | Abele et al. ................. | 606/46 |
| 6,039,733 A | * | 3/2000 | Buysse et al. ................ | 606/40 |
| 6,113,598 A | * | 9/2000 | Baker .......................... | 606/51 |
| 6,190,386 B1 | * | 2/2001 | Rydell ......................... | 606/51 |
| 6,273,887 B1 | * | 8/2001 | Yamauchi et al. ............ | 606/48 |
| 6,458,128 B1 | * | 10/2002 | Schulze ....................... | 606/50 |

* cited by examiner

*Primary Examiner*—Michael Peffley
*Assistant Examiner*—Peter J Vrettakos

(57) ABSTRACT

An electrosurgical instrument and technique for creating thermal seal or welds transected margins of engaged tissue. The working end provides very elongate jaws particularly suited for resecting tissue, such as in a lung resection. The jaw assembly carries a bi-polar electrode arrangement that provides for Rf current flow to targeted tissue described as a subfascial-to-fascial (or medial-to-surface) bi-polar approach. The working end of the device carries an openable and closable jaw assembly with paired first and second jaws for engaging tissue. The paired jaws have an axial channel for receiving a sliding (blade) member for transecting the captured tissue. The paired jaws carry electrode surfaces having a common polarity so that Rf current will not flow d between the jaws which engage the surface or fascial tissue layers. Further, the transecting member had flange-type surface portions that extend over a substantial longitudinal length of the jaws to maintain very high compression on captured tissue even when the jaws have a very small cross section and hence may be somewhat flexible.

11 Claims, 23 Drawing Sheets

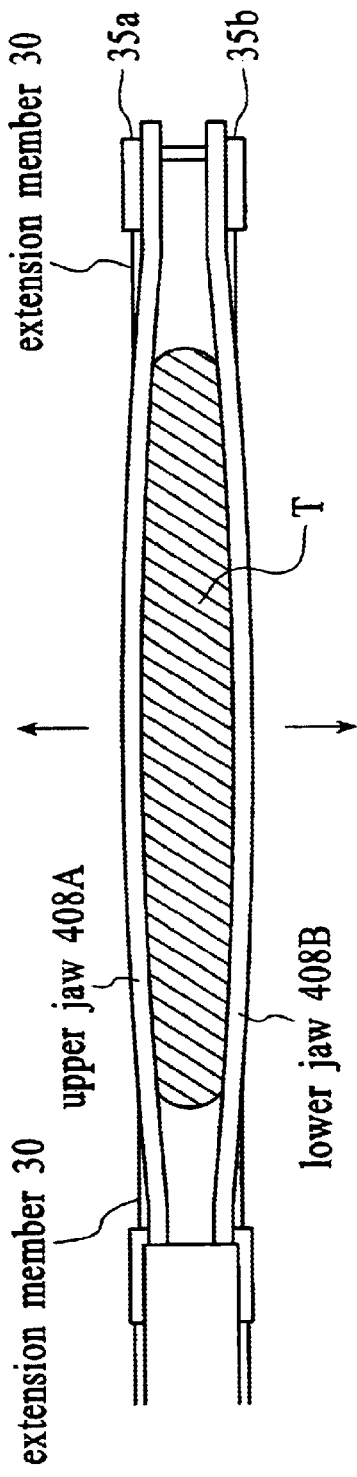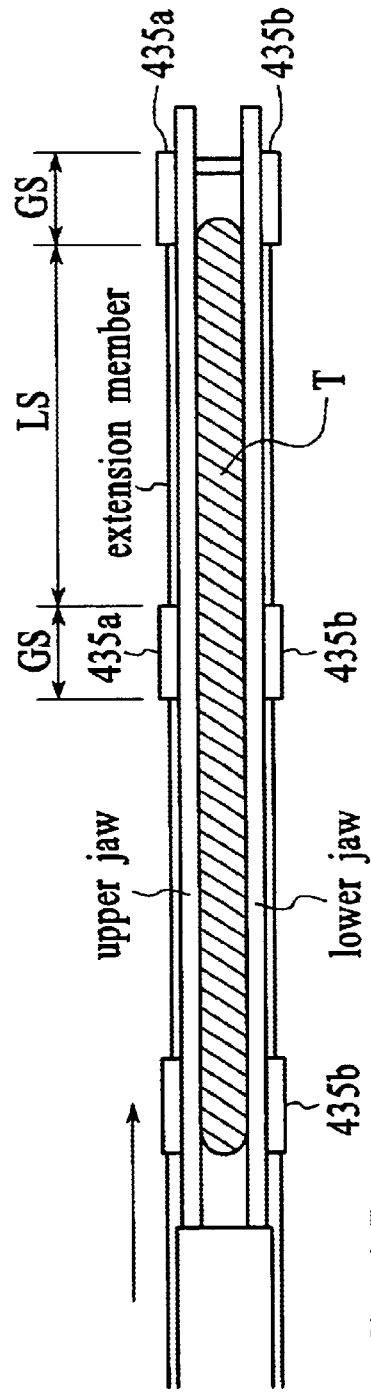
FIG. 13
FIG. 15

ELECTROSURGICAL SYSTEMS AND TECHNIQUES FOR SEALING TISSUE

CROSS-REFERENCE TO RELATED APPLICATIONS

This application claims priority from Provisional U.S. Patent Application Ser. No. 60/270,982 filed Feb. 23, 2001 titled Electrosurgical Systems and Techniques for Sealing Tissue, which is incorporated herein by this reference. This application is a Continuation-in-Part of U.S. patent application Ser. No. 09/694,233 filed Oct. 23, 2000 titled Electrosurgical Systems and Techniques for Sealing Tissue, which is incorporated herein by this reference.

BACKGROUND OF THE INVENTION

1. Field of the Invention

This invention relates to medical devices and techniques and more particularly relates to an electrosurgical jaw structure for thermally welding the margins of a transected tissue volume, as well as for providing highly elongate jaw members is a small cross-section that apply high compressive forces to Fred tissue.

2. Description of the Related Art

In various open and laparoscopic surgeries, it is necessary to seal or meld the margins of transected tissue volumes, for example, a transected blood vessel or a tissue volume containing blood vessels. In a typical procedure, a deformable metal clip may be used seal a blood vessel, or a stapling instrument may be used to apply a series of mechanically deformable staples to seal the transected edge a larger tissue volume. Such mechanical devices may create a seal that leaks which can result in later complications.

Various radiofrequency (Rf) surgical instruments for sealing transected structures have been developed For example, FIG. 1A shows a sectional view of paired electrode-jaws 2a and 2b of a typical prior art bi-polar Rf grasper grasping a blood vessel. In a typical bi-polar jaw arrangement, each jaw lace comprises an electrode and Rf current flows across the tissue between the first and second polarities in the opposing jaws that engage opposing exterior surfaces of the tissue. FIG. 1A shows typical lines of bi-polar current flow between the jaws. Each jaw in FIG. 1A has a central slot adapted to receive a reciprocating blade member as is known in the art for transecting the captured vessel after it is sealed While bi-polar graspers as in FIG. 1A can adequately seal or weld tissue volumes that have a small cross-section, such bi-polar instrument are often ineffective in sealing or welding many types of anatomic structures, e.g., (i) substantially thick structures, (n) large diameter blood vessels having walls with thick fascia layers f (see FIG. 1A), (iii) bundles of disparate anatomic structures, (iv) structures having walls with irregular fibrous content.

As depicted in FIG. 1A, a relatively large diameter blood vessel falls into a category that is difficult to effectively weld utilizing prior art instruments. A large blood vessel wall has substantially thick dense and non-uniform fascia layers underlying its exterior surface. As depicted in FIG. 1A, the fascia layers f prevent a uniform flow of current from the first exterior surface s to the second exterior surface s of the vessel that are in contact with electrodes 2a and 2b. The lack of uniform bi-polar current across the fascia layers f causes non-uniform thermal effects that typically result in localized tissue desiccation and charring indicated at c. Such tissue charring can elevate impedance levels in the captured tissue so that current flow across the tissue is terminated altogether.

FIG. 1B depicts an exemplary result of attempting to weld across a vessel with flick fascia layers f with a prior art bi-polar instrument. FIGS. 1A–1B show localized surface charring c and non-uniform weld regions w in the medial layers m of vessel. Further, FIG. 1B depicts a common undesirable characteristic of prior art welding wherein thermal effects propagate laterally from the targeted tissue causing unwanted collateral (thermal) damage indicated at d.

A number of bi-polar jawed instruments adapted for welding and transecting substantially small structures have been disclosed, for example: U.S. Pat. No. 5,735,848 to Yates et al.; U.S. Pat. No. 5,876,410 to Schulze et al.; and U.S. Pat. No. 5,833,690 to Yates et al. One other similar bi-polar instrument was disclosed by Yates et al. in U.S. Pat. No. 5,403,312. In that patent, paired bi-polar electrodes are provided in left and right portions of a jaw member to induce current flow therebetween. It is not known whether a jaw having the left-to-right or side-to-side bi-polar current flow of U.S. Pat. No. 5,403,312 was ever tested but it seems likely that such an instrument would confine current flow to the tissue's exterior surface and facial layers f (see FIG. 1B), thus aggravating the desiccation and charring of such surface layers.

What is needed is an instrument working end that can utilize Rf energy in new delivery modalities: (i) to weld a transected margin of a substantially thick anatomic structure; (ii) to weld or seal a margin of a blood vessel having thick or non-uniform fascia layers; (iii) to weld or seal tissue volumes are not uniform in hydration, density and collagenous content; (iv) to weld a transected margin of a bundle of disparate anatomic structures, and (v) to weld a targeted tissue region while substantially preventing collateral thermal damage in regions lateral to the targeted tissue.

SUMMARY OF THE INVENTION

The object of the present invention is to provide a novel technique—and an instrument working end capable of practicing the technique—for causing controlled Rf energy delivery and controlled thermal effects in a transected margin of tissues with thick facial layers, or other tissue with non-uniform fibrous content. For example, larger diameter blood vessels are a targeted application since such vessels have thick facials layers that can prevent uniform current flow and uniform resistive heating of the tissue.

As background, the biological mechanisms underlying tissue fusion by means of thermal effects are not fully understood. In general, the delivery of Rf energy to a captured tissue volume elevates the tissue temperature and thereby at least partially denatures proteins in the tissue. The objective is to denature such proteins, including collagen, into a proteinaceous amalgam that intermixes and fuses together as the proteins renature. As the treated region heals over time, the so-called weld is reabsorbed by the body's wound healing process.

In order to create an effective weld in a tissue volume with substantial fascial layers, it has been found that several factors are critical. The objective is to create a substantially even temperature distribution across the targeted tissue volume to thereby create a uniform weld or seal. Fibrous tissue layers (i.e., fascia) conduct Rf current differently than adjacent less-fibrous layers, and it is believed that differences in extracellular fluid contents in such adjacent tissues contribute greatly to the differences in electrical resistance It has been found that by applying very high compressive forces to a tissue volume comprising fascia layers and adjacent non-fibrous layers, the extracellular fluids either migrate from the non-fascial layers to the fascial layers or migrate from the captured tissue to collateral regions. In either event, high compressive forces tend to make the resistance more uniform regionally within the captured tissue volume. Further, it is believed that high compressive forces (i) cause protein denaturation at a lower temperature which is desirable, and (ii) cause enhanced intermixing of denatured proteins thereby creating a more effective weld upon tissue protein renaturation.

Also, it has been found that that a critical factor in creating an effective weld across adjacent fibrous (fascia) layers and non-fibrous (medial) layers is the deliver of bipolar Rf energy from electrode surfaces engaging the medial layers and the surface or fascia layers In other words, effective current flow through the fascia layers is best accomplished by engaging electrodes on opposing sides of the fascial layers. Prior art jaw structures that only deliver bi-polar Rf energy from outside the surface or fascial layers cannot cause effective regional heating inward of such fascial layers. For this reason, the novel technique causes Rf current flow to-and-from the medial (or just-transected) non-fascia layers of tissue at the interior of the structure, rather than to-and-from exterior surfaces only as in the prior art. This method is termed herein a medial-to-surface bi-polar delivery approach or a subfascia-to-fascia bi-polar approach.

Another aspect of the invention provides means for increasing the area of the engagement interface between an electrode and the just exposed medial tissue layers. This is accomplished by providing a wedge-like slidable member having an electrode surface for compressing the just-transected tissue volume against inner faces of the paired jaw members.

More in particular, the working end of he instrument carries a jaw assembly with paired first and second jaws for engaging and compressing tissue along a line targeted for transection. The transected tissue margins thereby expose medial tissue layers m that can be engaged by an electrode. The jaw structure is moveable between a fist (open) position and a second (closed) position by a slidable blade member that serves two functions: (i) to transect the captured tissue, and (ii) to contemporaneously lock together the elongate jaws by means of "I"-beam flanges that span both sides of the paired jaws.

The combination of the first and second jaws together with a cooperating slidable transecting (or blade) member further provides a novel electrode arrangement that can accomplish the electrosurgical welding technique of the invention. The opposing jacks carry electrodes sources coupled to an Rf generator that have a common polarity. In other words, Rf current does not flow directly from the first jaw to the second jaw (in contrast to prior art, see FIG. 1A). Rather, the extension portion of the slidable transecting member carries, or comprises, an electrode of an opposing polarity. Thus, when the transecting member is moved to the ended potion after transecting the engaged tissue volume, the elongate electrode carried by the transecting member will thus engage the medial or interior layers of the transected margin. By this means, for the first time, bipolar current flows can be directed from the transecting member that engages medial or subfascial tissue layers to both jaw faces that engage opposing surface or fascial tissue layers of the targeted tissue volume. It has been found that by engaging the medial portion of a just-transected structure with a first bi-polar electrode, and an exterior of the structure engaged with a second cooperating electrode, substantially uniform current flow through thick or non-uniform fascia layers can be accomplished This novel medial-to-surface bi-polar approach of the invention also seems to greatly reduce tissue charring, and substantially prevents collateral thermal damage in the tissue by reducing stray Rf current flow through tissue lateral to the engaged tissue.

Of particular interest, the invention provides other (optional) features that enhance the effectiveness of an medial-to-surface bi-polar approach. More in particular, it has been found that increasing the electrode engagement area with the medial tissue layers can enhance thermal effects for tissue welding For this reason, the elongate transecting member electrode may be configured as a wedge-type with an increasing cross-section that is adapted to plow into the medial tissue layers thereby increasing the electrode-tissue engagement area.

Also of particular interest, the invention provides means for highly compressing the engaged tissue between the electrode surface engagements, which has been found to assist in creating an effective weld. Such tissue compression is accomplished by using a flanged transecting member that compresses and maintains the jaws in a closed position over the entire length of the jaws In another embodiment of the invention, the jaw assembly further includes components of a sensor system which together with a power controller can control Rf energy delivery during a tissue welding procedure. For example, feedback circuitry for measuring temperatures at one or more temperature sensors in the jaws may be provided Another type of feedback circuitry may be provided for measuring the impedance of tissue engaged between the transecting member and a jaw. The power controller may continuously modulate and control Rf delivery in order to achieve (or maintain) a particular parameter such as a particular temperature in tissue, an average of temperatures measured among multiple sensors, a temperature profile (change in energy delivery over time), or a particular impedance level or range.

Additional objects and advantages of the invention will be apparent from the following description, the accompanying drawings and the appended claims.

BRIEF DESCRIPTION OF THE DRAWINGS

FIG. 7A being a sectional view of a large blood vessel with thick fascia layers being (i) captured and compressed by the jaw structure, and (ii) being transected by the leading edge of the blade member, FIG. 7B being a sectional view of the increased diameter of an extension member electrode engaging a broad surface of the medial tissue layers as such layers are compressed outwardly against the cooperating jaw faces.

FIG. 8A being an illustration of Rf current flow from electrodes in contact with medial tissue layers to electrodes in contract with surface tissue layers; and FIG, 8B being an illustration of the thermal weld effects caused of the novel form of bi-polar current flow of FIG. 8A.

FIG. 13 is a longitudinal sectional view of an exemplary elongate jaw structure illustrating the problem of jaw flex.

FIG. 15 is a longitudinal sectional view similar to FIG. 13 showing the extending member of FIG. 14 in operation.

DETAILED DESCRIPTION OF THE INVENTION

Figure 1A:
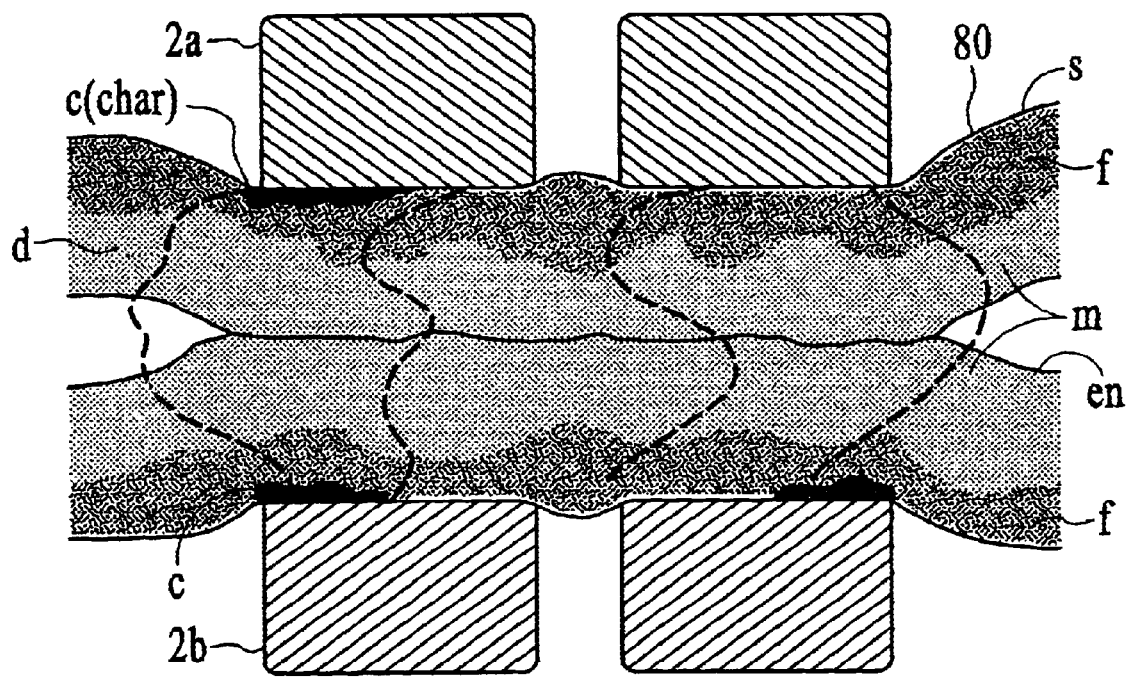
FIG. 1A is an illustration of current flow between the paired jaws of a prior art bi-polar radiofrequency device in a method of sealing a large blood vessel having substantially thick fascia layers.
Figure 1B:
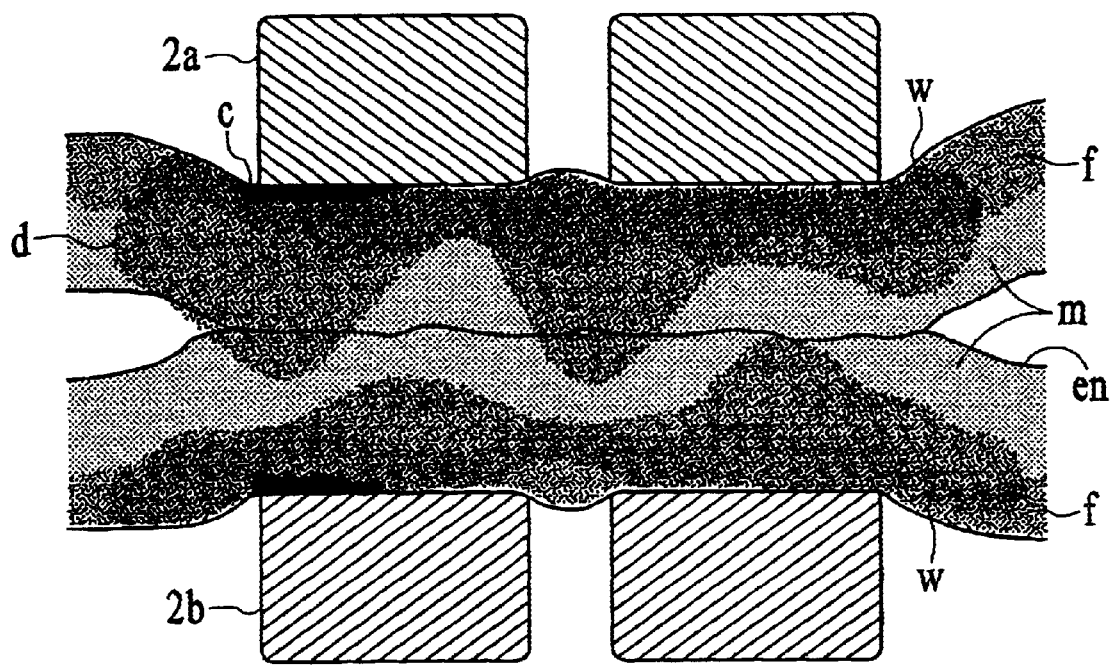
FIG. 1B illustrates representative weld effects of the bi-polar current flow of FIG. 1A.
Figure 2:
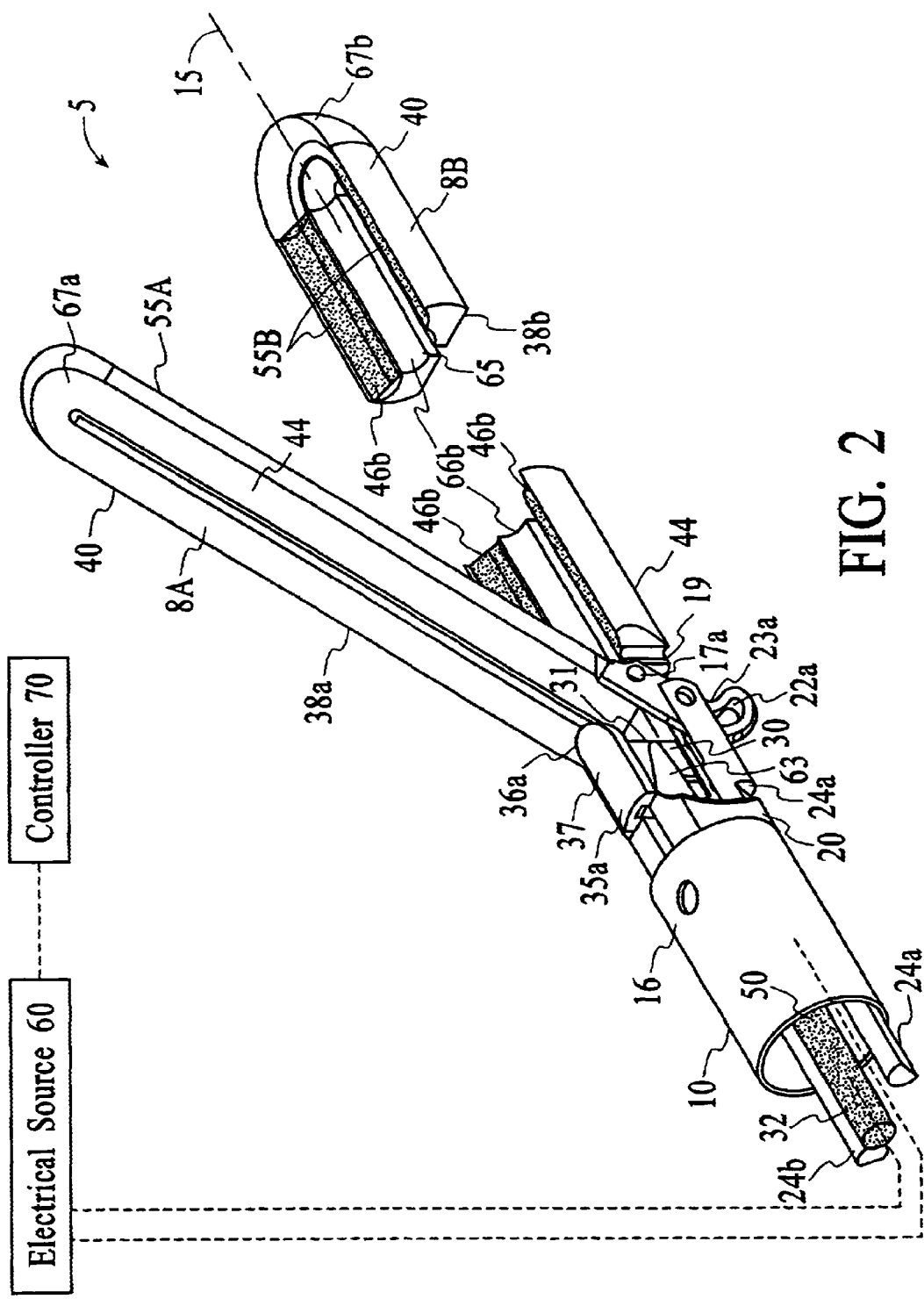
FIG. 2 is a perspective cut-away view of the Rf working end of the present invention with the cooperating jaw members in a first (open) position and a sliding transecting or blade member in a first (retracted) position.

1. Type "A" Electrosurgical Working End for Sealing or Welding Tissue. Referring to FIG. 2, the working end 5 of an exemplary Type "A" embodiment is shown that is adapted for sealing or welding a tissue volume, such as a blood vessel, in an open or endoscopic procedure. The working end 5 has paired jaw portions 8A and 8B that are carried at the distal end of elongate introducer portion 10 (with handle not shown) extending along central longitudinal axis 15. In this exemplary embodiment, the structural component of introducer portion 10 has a cylindrical cross-section and comprises a th in-wall tubular sleeve 16 that extends from a proximal handle (not shown). The diameter of sleeve 16 may range from about 3 mm. to 10 mm., e.g., to cooperate with a standard endoscopic trocar sleeve. The handle may be any type of pistol-grip or other type of handle known in the art that carries actuator levers or slides as described below.

Figure 3:
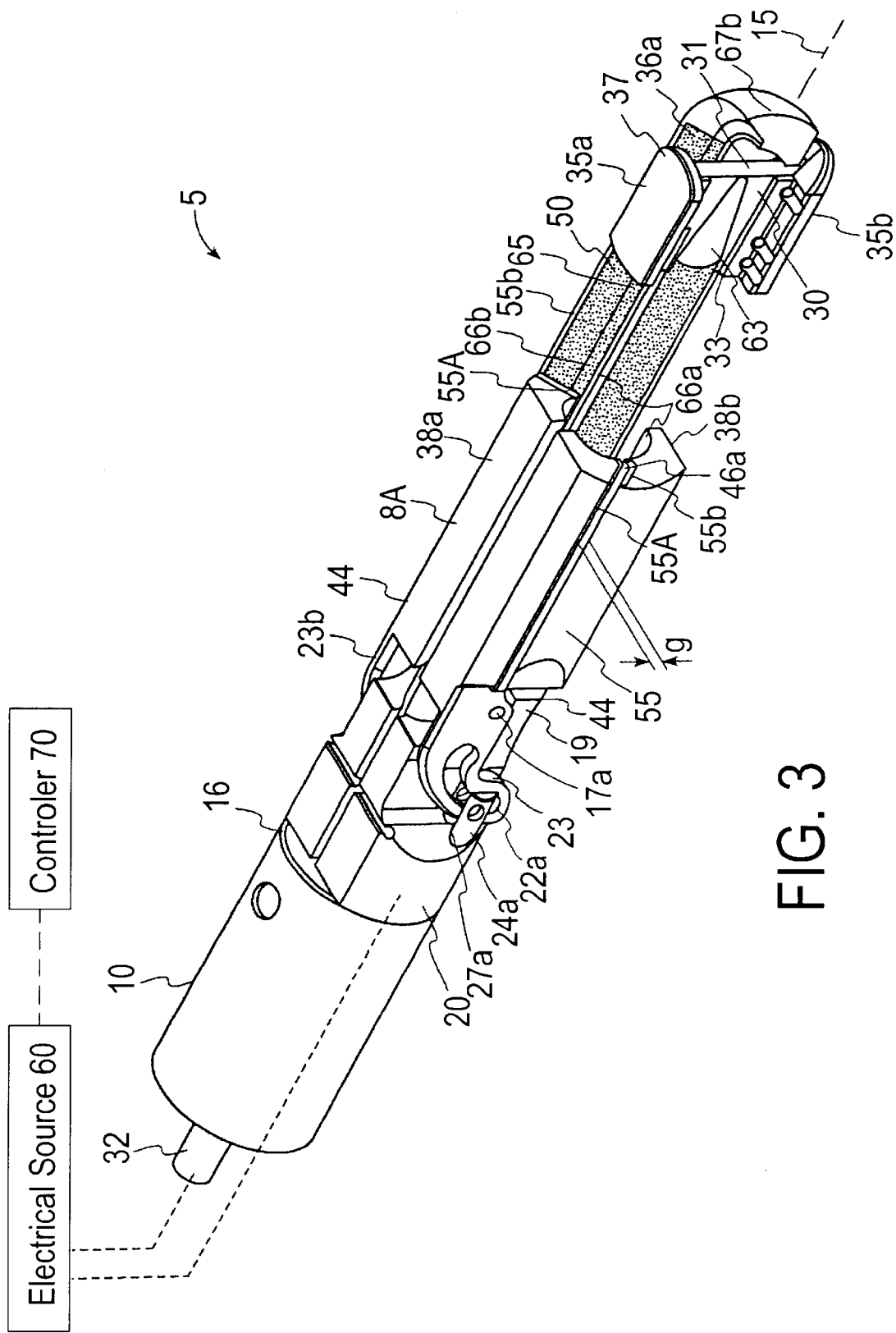
FIG. 3 is a different perspective cut-away view of the working end of FIG. 2 with the cooperating jaw members in a second (closed) position and the sliding transecting member in second (extended) position.

The first jaw member 8A is actuated from the first open position of FIG. 2 to the second closed position of FIG. 3 by a novel jaw-closing system that applies very high compressive forces to captured tissue volumes over the length of substantially elongate jaws. Referring to FIG. 2, it can be seen that the upper (first) jaw member 8A is actuatable about pivot pins 17a and 17b to open and close relative to the lower (second) jaw member 8B that in this exemplary embodiment is configured as a fixed (non-actuatable) jaw. The pivot pins 17a and 17b are fit into a proximal portion 19 of lower jaw body member 20 that is fixedly coupled to the distal end of thin-wall sleeve 16.

In this embodiment, the jaw structure is moved from the first open position (FIG. 2) to the second closed position (FIG. 3) by a dual-actions jaw-closing system. In FIG. 2, it can be seen that upper jaw member 8A has arcuate slots 22a and 22b in arm portions 23a and 23b. Reciprocatable actuator rods 24a and 24b carry pins 26a and 26b in their distal ends that slide in arcuate slots 22a and 22b of the jaw arms to initially actuate upper jaw 8A toward a closed position (FIG. 3) from the open position of FIG. 2. It can be seen that the slidable actuator rods 24a and 24b comprise a first component of the jaw-closing system. The proximal ends of actuator rods 24a and 24b are coupled to a first actuator known in the art and carried in the handle portion (e.g., a lever arm or squeeze grip) that translates the rods to and fro. These rods 24a anti 24b slide through parallel aligned bores 27a and 27b in body member 20. This first mechanism for actuating upper jaw 8A is adapted to cause an initial movement of the jaw toward the second closed position (see FIG. 3). A second actuator mechanism, described below, is provided for locking the paired elongate jaws in the second closed position (FIG. 3) to provide high tissue compressing forces over the entire length of the elongate jaws, and to open the jaws. The axial length of jaws 8A and 8B indicated at a may be any suitable length depending on the anatomic structure targeted for transection and sealing and may range from about 100 mm. or more, for example for resecting and sealing lung, to as little as 5.0 mm. for a micro-surgery.

Figure 4:
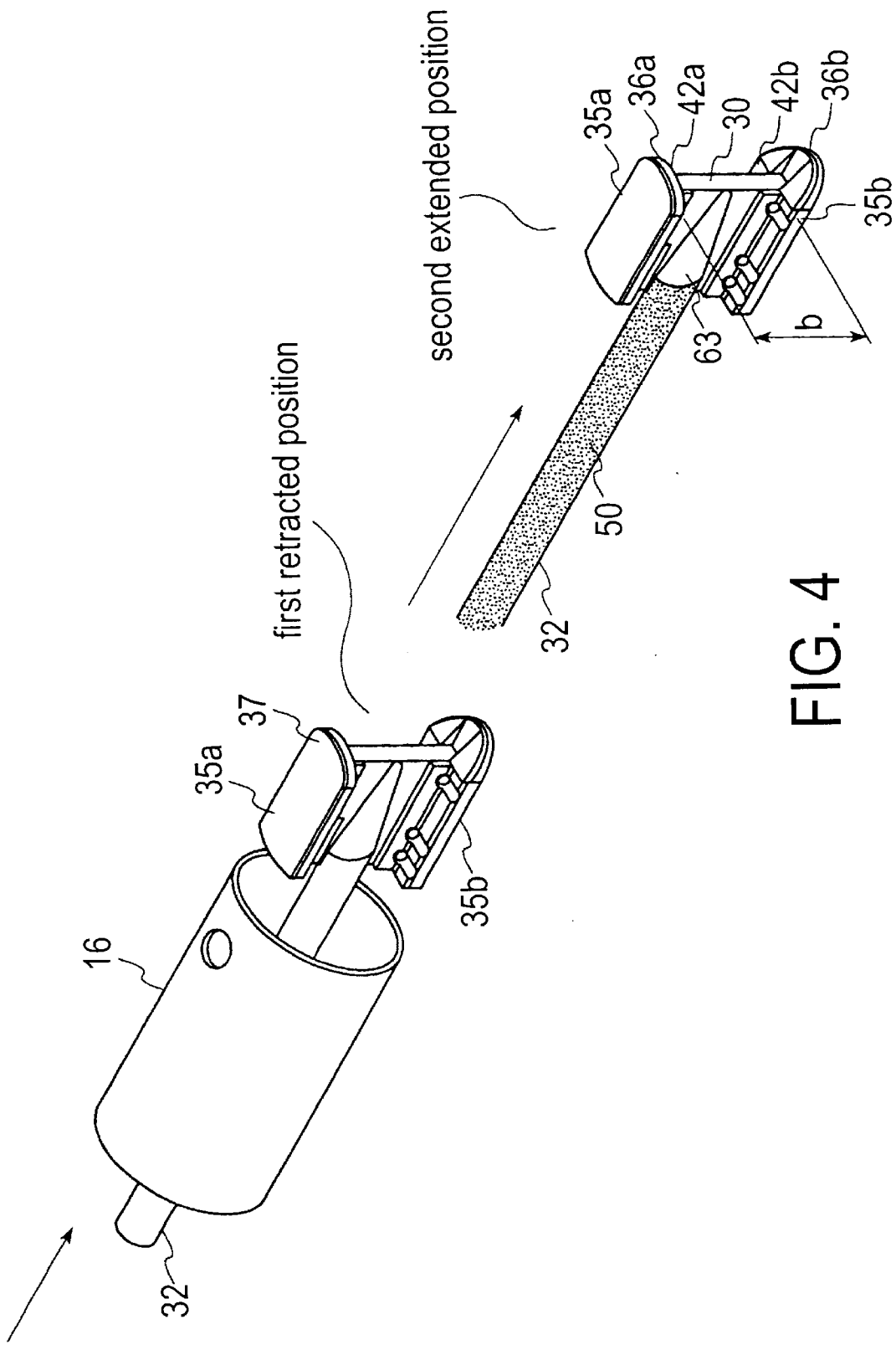
FIG. 4 is a perspective view of the slidable blade member of the working end of FIGS. 2–3 in first and second positions with the jaw members not shown.
Figure 5A:
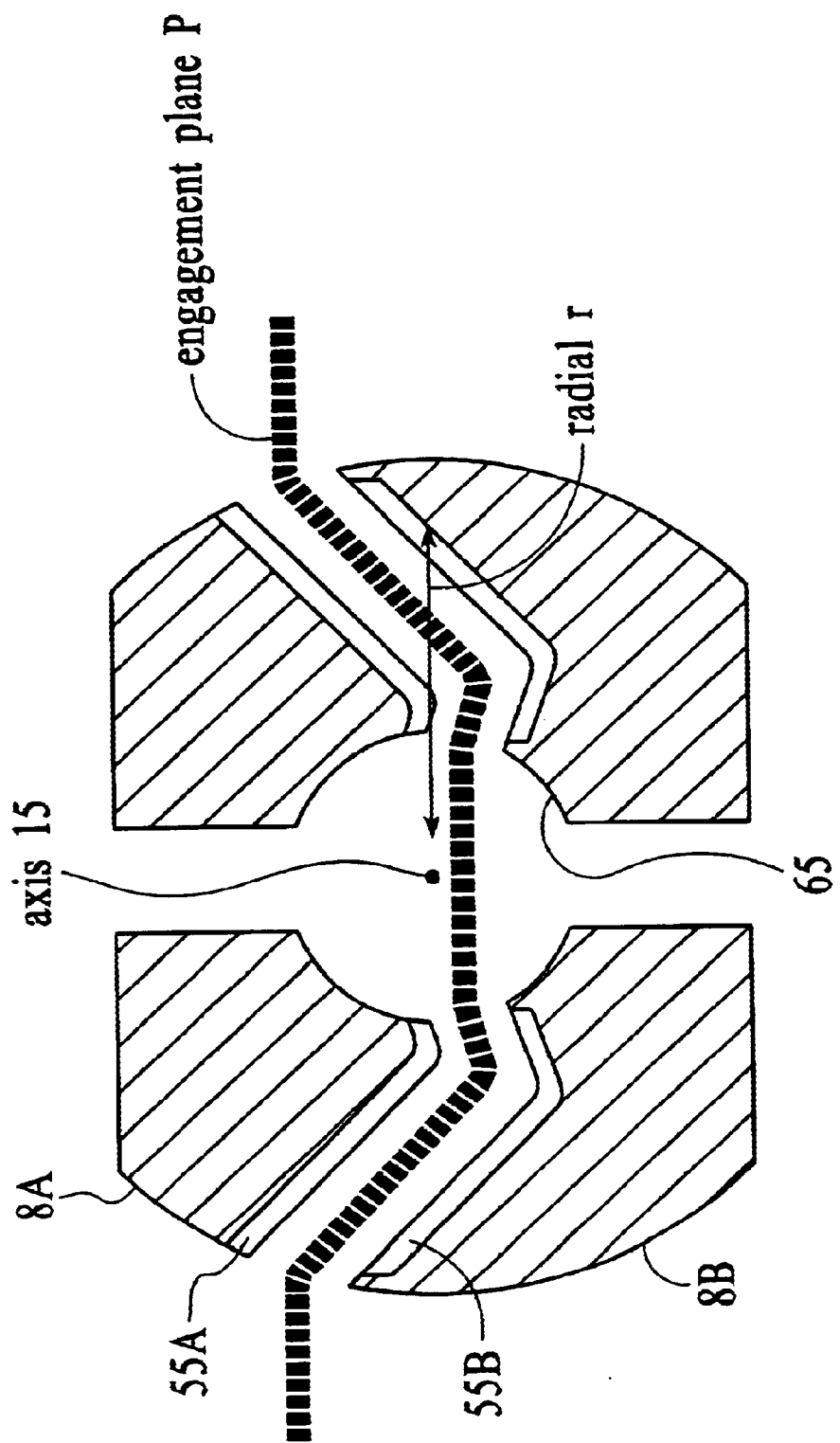
FIG. 5A is an enlarged cross-sectional view showing an exemplary shape of the jaw faces of FIG. 2 taken along line 5A—5A and depicting a tissue engagement plane.

As can be seen in FIG. 2, the upper and lower jaws 8A and 8B have axial slots therein indicated at 28a and 28b that cooperate to receive a thin translatable blade member 30 with sharp edge 31 for transecting tissue captured in the jaw assembly. To better explain the second mechanism for closing the jaws, FIG. 4 shows introducer sleeve 16 with blade member 30 (without showing jaws) in its first retracted position and its second extended position. The proximal end of extension member 32 (not shown) is coupled to a second actuation means known in the art and carried in the handle portion (not shown) of the device to translate blade member 30 dinghy and proximally. The actuator may be any type of lever arm or slider adapted to translate the blade member. The distal end 33 of extension member 32 is connected to the blade member. The blade portion of the assembly of FIG. 4 has an "I"-beam type cross-section 37 with upper flange member 35a and lower flange member 35b. Of particular inter as will described below, the upper and lower flanges 35a and 35b serve as functional components of the dual-action jaw-closing mechanism. The upper and lower flanges 35a and 35b are fixed to blade member 30 by any suitable means such as fittings with pins, adhesives or the like. Further, as can be seen in FIGS. 2 and 4, the rounded leading edge 36a of upper flange portion 35a is adapted to push against flat surface 38a of upper jaw 8A as a cam to thus push the jaw toward the closed position of FIG. 3. Besides being adapted to push moveable jaw 8A toward the closed position, it can be understood that the paired upper and lower flanges 35a and 35b are adapted to lock the distal portions 40 of the jaws in the second closed position. As can be seen in FIG. 4 and FIG. 5A, the inner faces 42a and 42b of flanges 35a and 35b of the "I"-beam form 37 are spaced apart a fixed dimension and are thus adapted to engage against outer surfaces 38a and 38b of the jaws to thereby lock the distal jaw portions 40 together. The dimension (indicated at b in FIG. 4) between flange inner faces 42a and 42b determines and controls the thickness of the tissue that is compressed between the jaw faces. In sum, the proximal jaw portions 44 (FIG. 3) are maintained together by the pivot pins 17a and 17b to define a predetermined gap dimension g between jaw face portions 46a and 46b in, the closed position, while the distal jaw portions 40 are locked together by the flanges of the blade member. The combination blade and jaw-locking mechanism built into the blade member 30 (see FIG. 4) allows very elongate jaws to be locked together at distal ends thereof to thereby apply high compressive forces to captured tissue—which forces could not be achieved with a conventional jaw-closing mechanism as used is prior art graspers. This fist and second jaw-closing mechanisms are preferably actuated from a single suitable actuator (e.g., a lever arm or squeeze grip) that (i) can move actuator rods 24a and 24b proximally to initiate the jaw closing process, and (i) move the extension member 32 coupled to blade member 30 distally to close and lock the jaws in the second closed position (see FIG. 3). Such dual-actuation mechanical systems are known in the art and need not be described in detail herein.

Referring to FIG. 4, other novel features and functions of the blade member or assembly can now be described In this preferred embodiment, the extension member 32 of the blade assembly has a surface comprising an electrode 50 that is of any suitable conductive material. As will be described below, this core electrode or central electrode 50 is adapted to cooperate with electrodes 55A and 55B in the upper and lower jaws, respectively. The core electrode 50 is coupled to electrical source 60 by a lead wire indicated at 62 in FIGS. 2–3. As can be seen best in FIG. 4, the extension member 32 has a distal tapered portion 63 that is fixedly coupled to blade member 30. The tapered portion 63 rapidly transitions to a greater cross-sectional medial portion 64 of extension member 32 that serves a compression member to press transected tissue outwardly against cooperating faces 66a and 66b of the jaws. In this embodiment, the cross-section of extension member 32 and electrode 50 is round, but it should be appreciated that any shape is possible that is designed to cooperate with the shape of cooperating jaws faces to compress tissue in the method of the invention described below. This core electrode 50 is adapted to contact and engage the inner or medial layers m of just-transected tissue, as well as to laterally compress the just-transected tissue against jaw faces 66a and 66b, as will be described the practice of the method of the invention.

Now turning to FIG. 5A, the novel shapes and surfaces of electrodes faces 55A and 55B in engaging faces 46a and 46b of jaws 8A and 8B can be described. FIG. 5A shows that the paired jaws in the second closed position generally define an open central channel portion indicated at 65 that has a cross-sectional shape that cooperates with the cross-sectional shape of core electrode 50 phantom view), in this case having a round cross-section. The distal ends 67a and 67b of jaws 8A and 8B extend around, and define, the distal end open channel 65 within the closed jaws as can be seen in FIG. 3.

Figure 5B:
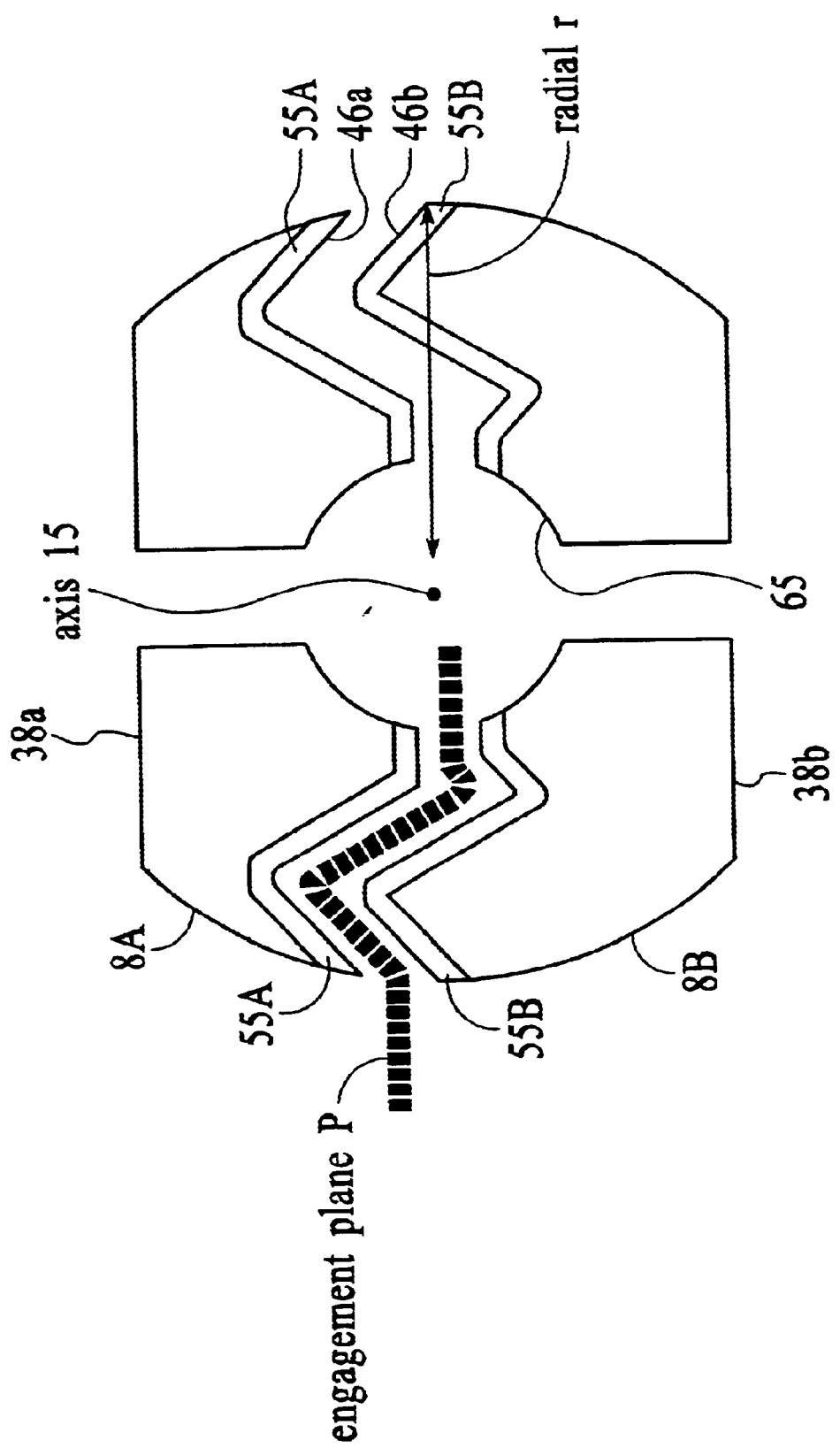
FIG. 5B is an alternative cross-sectional shape (similar to FIG. 5A) of jaw faces defining an alternative engagement plane.
Figure 6:
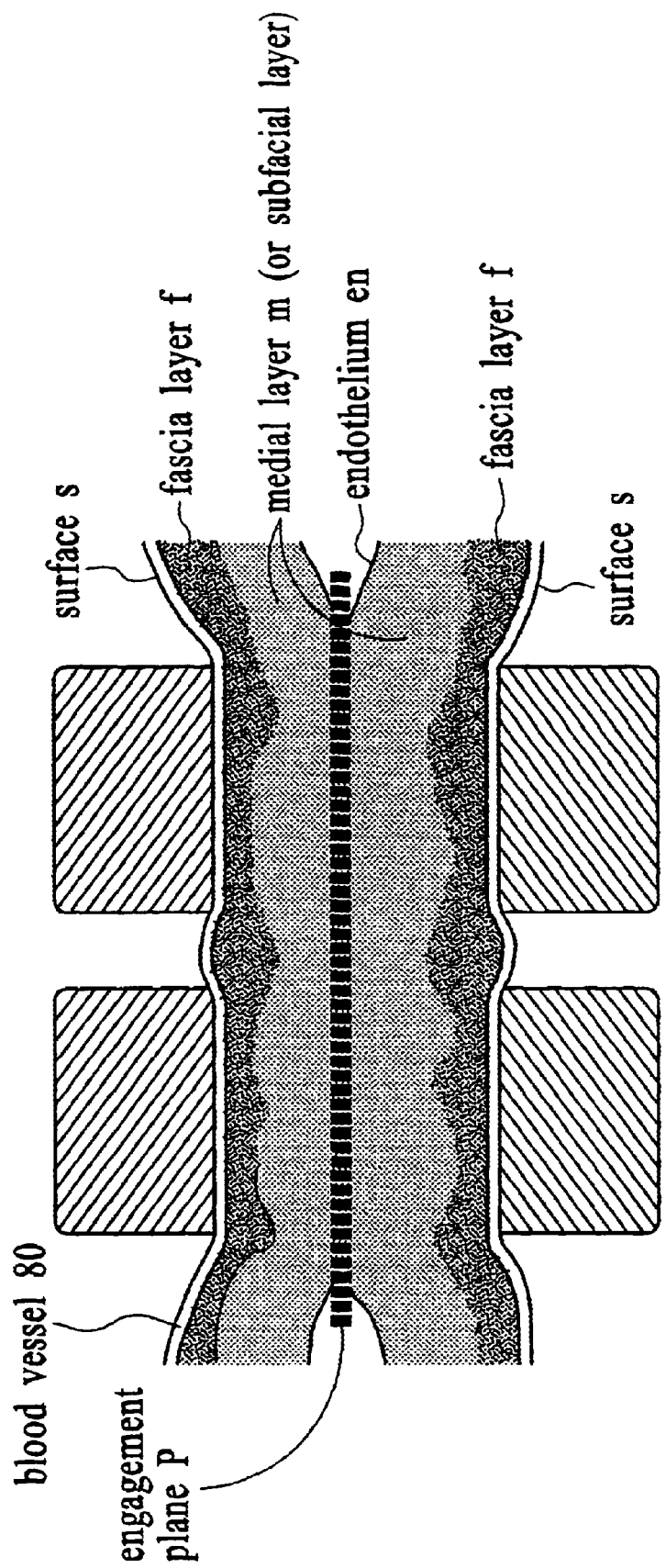
FIG. 6 is a view of the shape of the engagement plane of a prior art electrosurgical jaw wherein the jaw faces extend generally as a radial of the central axis.

FIG. 5A her shows that engaging faces 46a and 46b of jaws 8A and 8B define an engagement plane P (dashed line) that represents. the plane in which targeted tissue is captured or engaged between the jaws before being transected by blade 30, as well as during Rf energy delivery. Of particular interest, the engagement plane P: (i) has a non-linear form or non-planar from transverse to central axis 15 of the jaw structure, and/or (ii) has no portions that comprise a radial r of the axis 15 of the jaws (see FIG. 5A). In prior art jaws, such an engagement plane P of the jaws typically is linear and also comprises a radial of a central axis of the jaws as shown in FIG. 6. By the term radial, it is meant that a radial line or plane is orthogonal to the central axis of the jaws and also be termed a radius (see FIG. 6). As can be seen in FIG. 6, such a radial r thus defines the shortest possible distance from central axis 15 to an exterior surface or edge of the jaw structure. In the present invention, it has been found that thermal welds are enhanced in medial-to-surface Rf current flows when increased electrode surface areas are provided for engaging tissue between the upper and lower jaws. The novel manner of providing such increased electrode engagement area, within a small diameter jaw form, is to not provide an engagement plane P that is a simple radial r of central jaw axis. Rather, the preferred embodiment of the invention provides non-radial forms for such an engagement plane P. As can be seen in FIG. 5A, a preferred engagement plane P is provided that extends at angles to a radial r thereby providing an increased dimension across the jaw faces 46a and 46b that carry the surfaces of electrodes 55A and 55B. While FIG. 5A depicts an engagement plane P that is suitable for accomplishing the method of the invention, FIG. 5B depicts another engagement plane P that has jaw faces 46a and 46b that define an undulating form and thus is somewhat further removed from a radial form.

The sharp leading edge 31 of blade 30 shown in FIG. 4 is preferred for cutting tissue. Alternatively, the leading edge of blade member 30 may be an electrode element that operates at high Rf intensities suitable for cutting tissue as is known in the art. For example, for tissue cutting purposes, Rf frequencies may range from 500 kHz to 2.5 MHz, with power levels ranging from about 50 W. to 750 W., and open circuit voltages ranging as high as 9 Kv. In this alternative configuration, such an electrode cutting element preferably is insulated from core electrode 50 that cooperates with paired electrodes 55A and 55B. Alternatively, the working end may have a singular electrode that is adapted to both transect the captured tissue and thereafter cooperate with electrodes 55A and 55B to seal the tissue as will be described below.

Figure 7A:
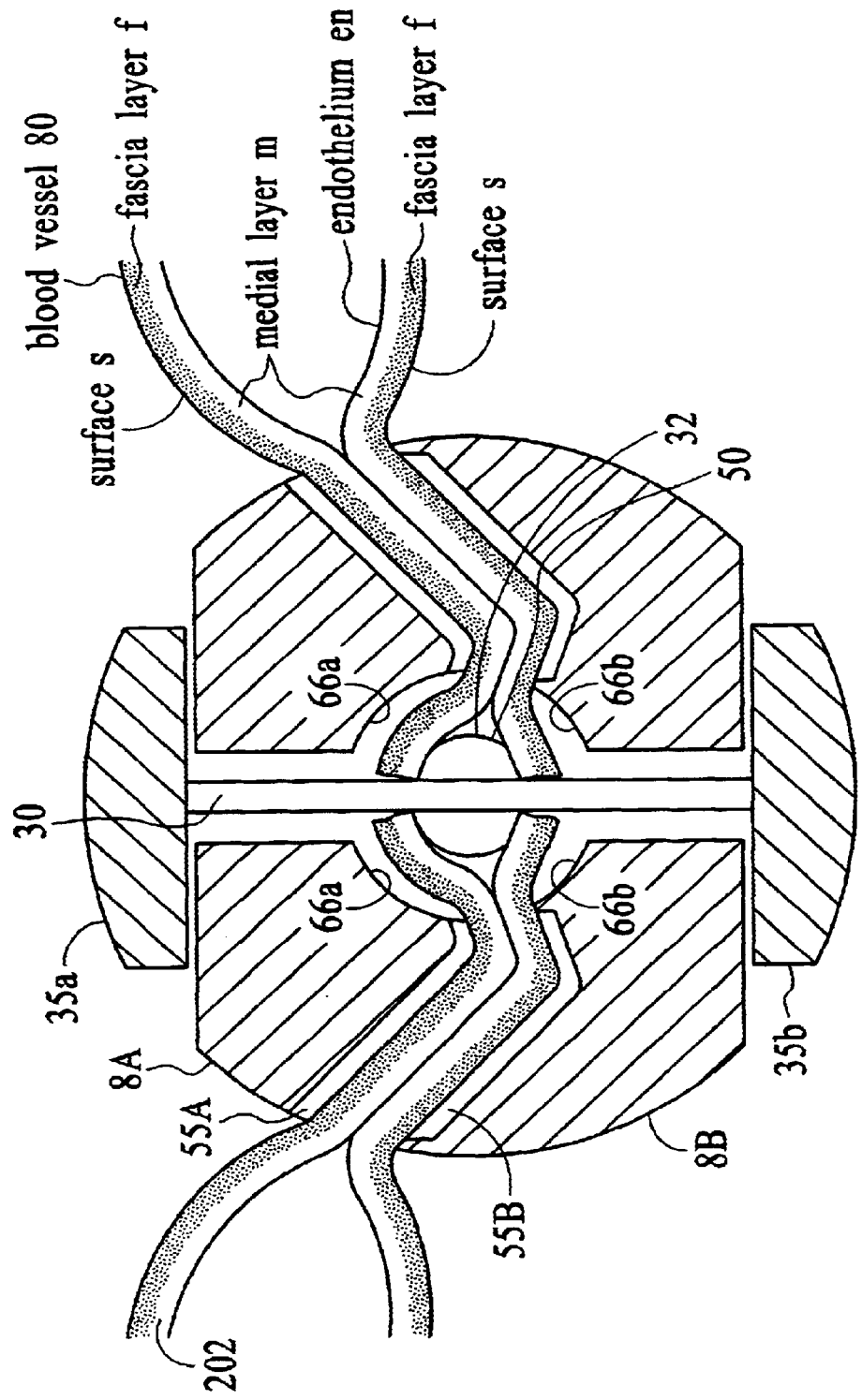
FIGS. 7A–7B are sectional illustrations of steps of practicing the method of the invention in moving a jaw assembly to a closed position to provide high compressive forces in providing substantial electrode contact with surface layers and medial layers of the engaged tissue.
Figure 7B:
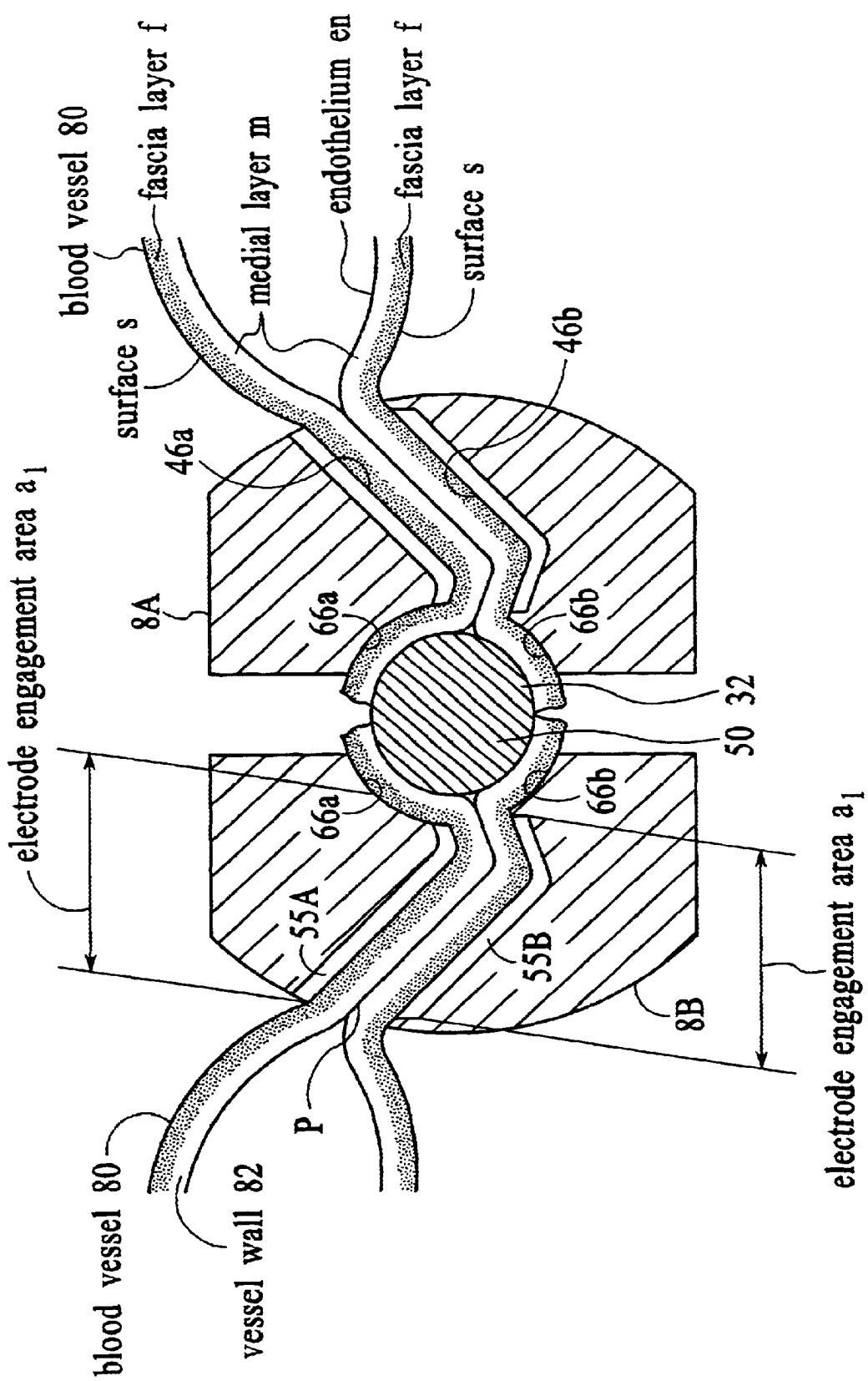

Of particular interest, it can now be seen the translation of medial portion 64 of the extension member 32 provides tissue-compressing means for compressing a medial portion m of the transected and exposed margin of the anatomic structure between cooperating surfaces. More in particular, FIGS. 7A–7B illustrate sectional views of the exemplary cross-sectional shape formed into engaging is 66a and 66b of central channel 65 of the jaws and central electrode 50. Referring back to FIG. 4, it can be seen that extension member 32 and the surface of electrode 50 increase in cross-sectional dimension, from distal taper portion 63. Thus, the extension member 32, besides functioning to compress the medial tissue m of the vessel walls outwardly against the inwardly-facing jaw faces 66a and 66b, also functions to increase the surface area of electrode 50 in contact with medial tissue layers m of the transected structure. As shown schematically in FIGS. 7A–7B, electrodes 55A and 55B in the paired jaws have a common (first) polarity and are coupled to electrical generator 60 and controller 70. The cooperating central electrode 50 carried by extension member 32 has an opposing (second) polarity, and again is coupled to generator 60 and controller 70. FIG. 7B thus indicates that bi-polar Rf current will flow between the cent extension member electrode 50 and either jaw face 46a and 46b (i.e., electrodes 55A and 55B carried therein). The views of FIGS. 2 and 3 indicate that a current-carrying wire lead 62 emends from electrical source 60 to extension member electrode 50. Leads 74a and 74b extend from Rf source 60 to each of electrode elements 5A and 55B carried within the jaws. The electrodes are of any suitable material such as aluminum, stainless steel, nickel titanium, platinum, gold, or copper. Each electrode surface preferably has a micro-texture (e.g., tiny serrations or surface asperities, etc.) for better engaging tissue and for delivering high Rf energy densities in engaged tissues as is known in the art. The bi-polar Rf current may be switched on and off by a foot pedal or any other suitable means such as a switch in handle (not shown).

Another embodiment of the invention (not shown) includes a sensor array of individual sensors (or a single sensor) carried in any part of the jaw assembly that is in contact with the tissue targeted for welding. Such sensors preferably are located slightly spaced apart from electrodes 55A–55B for the purpose of measuring temperatures of tissue adjacent to the electrodes during a welding procedure. It should be appreciated however that the sensors also may measure temperature at the electrodes. The sensor array typically will consist of thermocouples or thermistors (temperature sensors that have resistances that vary with the temperature level). Thermocouples typically consist of paired dissimilar metals such as copper and constantan which form a T-type thermocouple as is known in the art. Such a sensor system can be linked to feedback circuitry that together with a power controller can control Rf energy delivery during a tissue welding procedure. The feedback circuitry can measure temperatures at one or more sensor locations, or sensors can measure the impedance of tissue, or voltage across the tissue, that is engaged between the transecting member and a jaw. The power controller then can modulate Rf delivery in order to achieve (or maintain) a particular parameter such as a particular temperature in tissue, an average of temperatures measured among multiple sensors, a temperature profile (change in energy delivery over time), a particular impedance level or range, or a voltage level as is known in the art.

Operation and use of the working end 5 of FIGS. 2–3 in performing a method of the invention can be briefly described as follows. FIG. 7A shows a targeted tissue volume t that is captured between first and second jaws SA and 8B. The targeted tissue t may be any soft tissue or anatomic structure of a patient's body and FIGS. 7A–7B depict a large diameter blood vessel 81 with vessel walls 82 having thick fascia layers indicated at f underlying exterior surfaces s, medial tissue layers m and endothelial layers en. FIG. 7A depicts the blood vessel as it is transected by blade member 30. FIG. 7A further shows the paired electrodes 55A and 55B of first and second jaw faces 46a and 46b engaging exterior surfaces s of the targeted tissue t thereby defining electrode engagement areas indicated at $e_1$ (collectively) between the first polarity electrodes 55A–55B and the exterior surfaces s of the vessel.

Referring to FIG. 7B, it can be easily understood that progressive slidable movement of blade 30 causes the increased cross-section of core electrode 50 to plow into walls 82 of the vessel to press the medial tissue m between the extension member 32 and tie cooperating sides 66a and 66b of axial channel 65 in the opposing jaw members. At the same time, the slidable extension member 32 carries electrode surface 50 that is pressed into contact with the endothelium en and medial tissue volumes m to thereby provide a broad engagement surface indicated at $e_2$ between the second polarity core electrode 50 and such medial tissue m (defined as including endothelium en). In FIG. 7A, the electrodes 55A and 55B are shown as being insulated from the structural component of jaws, but it should be appreciated that these electrodes 55A and 55B may comprise the structural component of the jaws, for example in very small instruments. Thus, in such an embodiment, the electrode engagement sure area $e_1$ of electrodes 55A and 55B can comprise substantially the entire jaw face that contacts the targeted tissue.

Figure 8A:
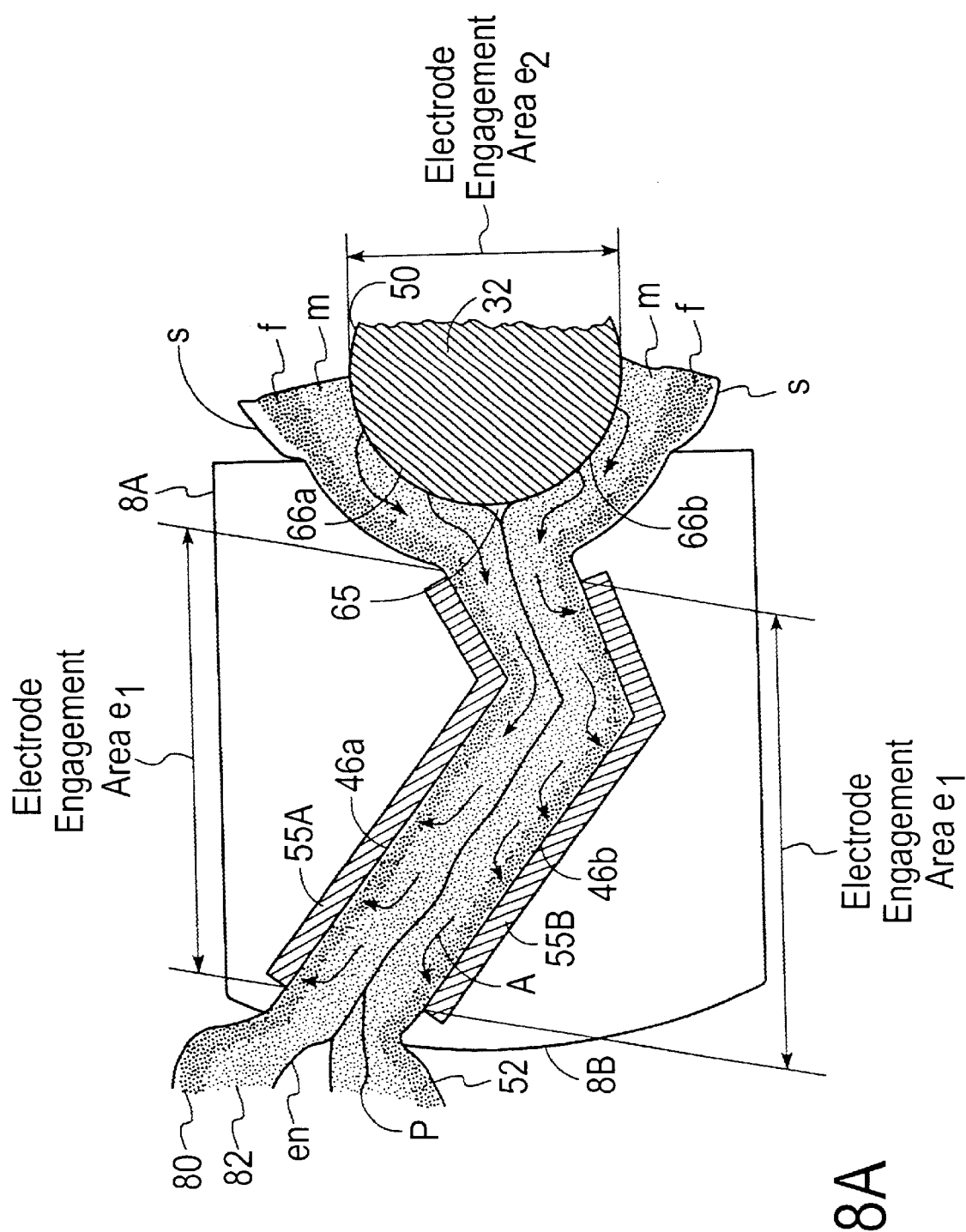
FIGS. 8A–8B are sectional illustrations of steps of practicing the method of delivering bi-polar Rf current flow to seal or weld the transected margins the engaged blood vessel of FIGS. 7A–7B.
Figure 8B:
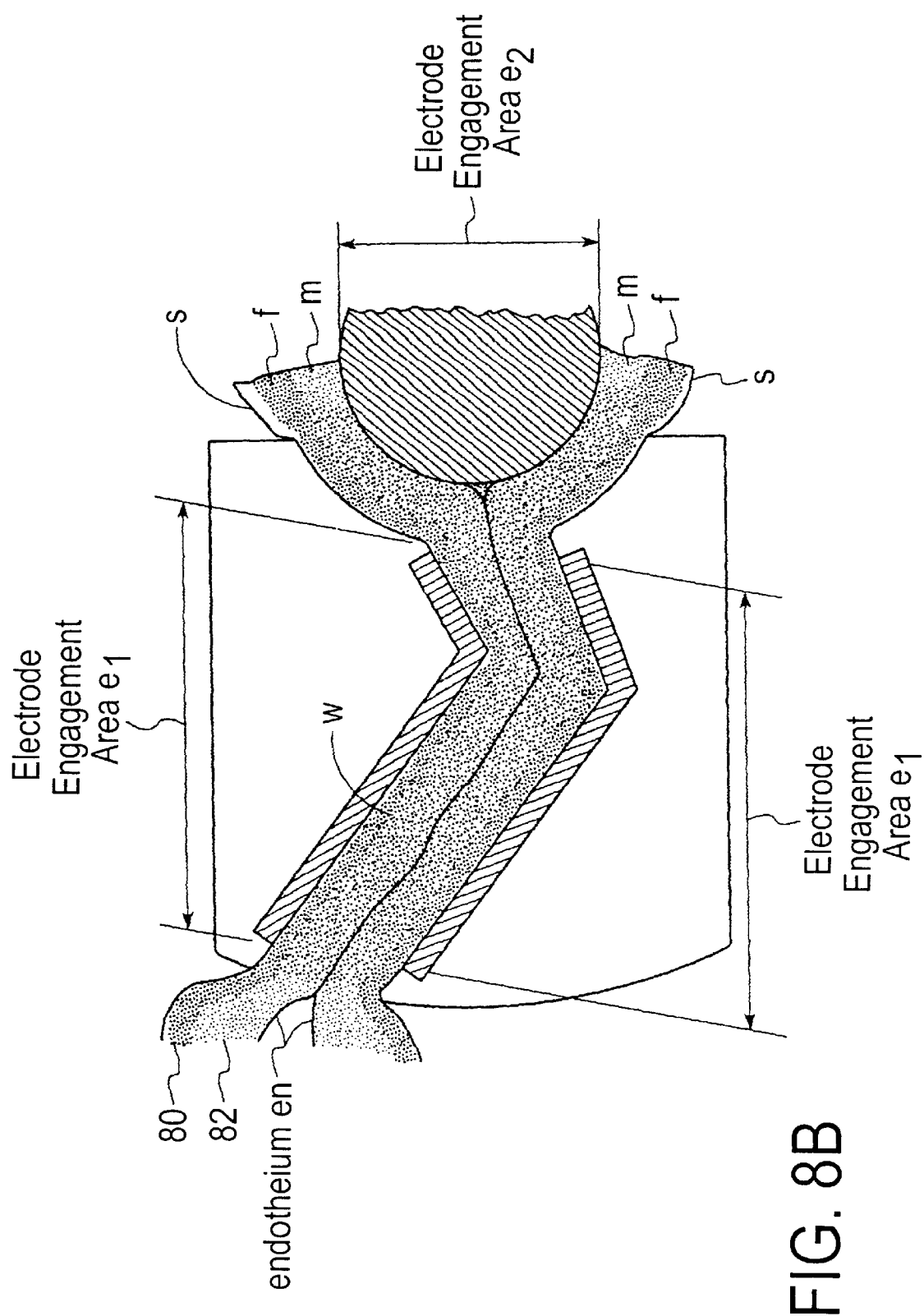

Now turning to FIG. 8A, an illustration is provided that indicates the sealing or welding effect that is achievable by the medal-to-surface bi-polar current flow (or vice versa) indicated by arrows A. It has been found that a substantially uniform weld w can be created across the entire tissue volume captured between the engagement surfaces $e_1$ and $e_2$ of the jaw electrodes 55A–55B and central electrode 50, respectively. In other words, the sectional illustration of FIG. 8B shows that a weld w can be created where the proteins (including collagen) are denatured, intermixed under high compressive forces, and then permanently fused upon cooling to seal or weld the margin of the transected vessel. Further, it is believed that the desired weld effects can be accomplished substantially without collateral thermal damage to adjacent tissues indicates at 92 in FIG. 8B.

Figure 9A:
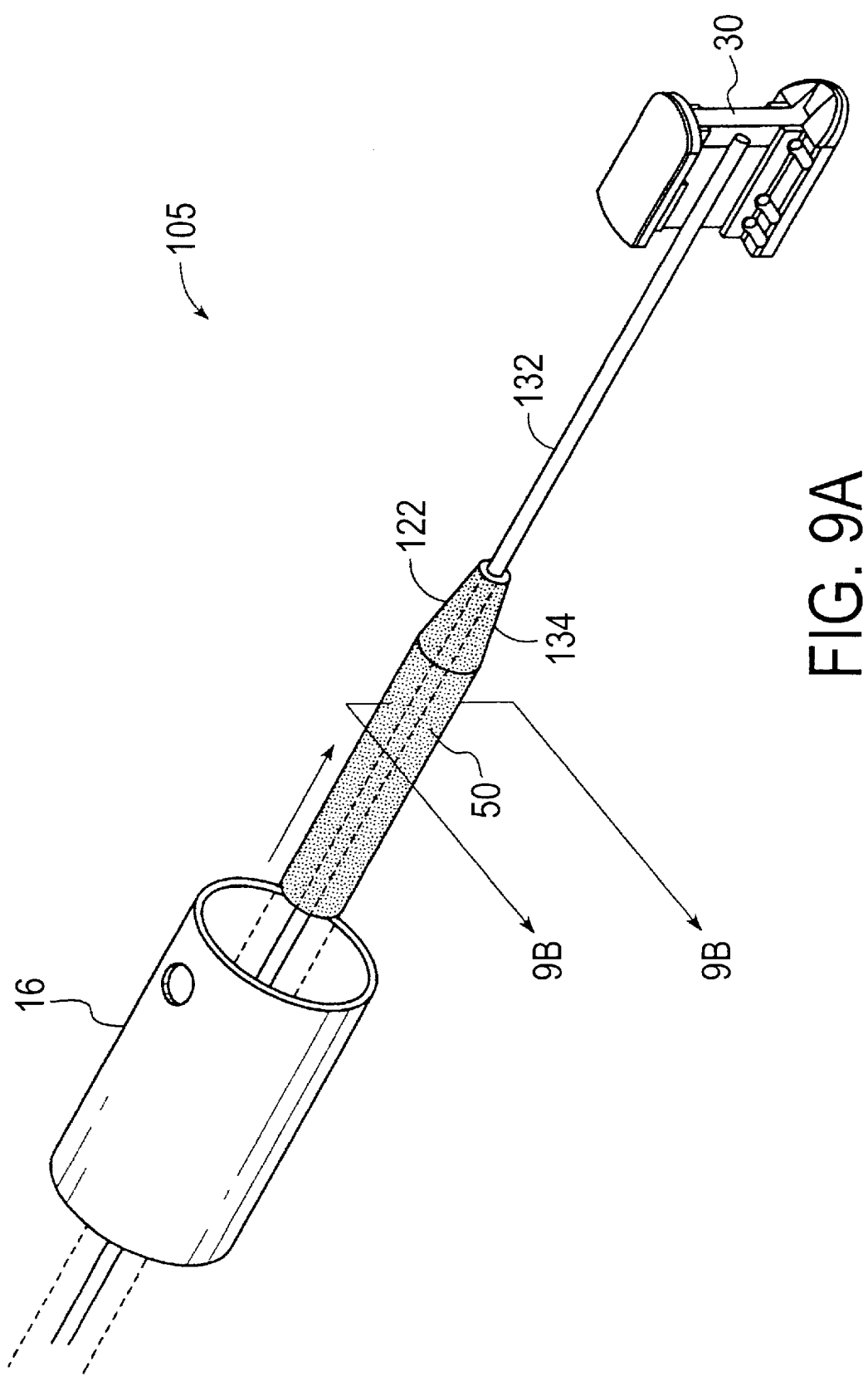
FIG. 9A is a perspective view of a Type "B" embodiment of electrosurgical working end (similar to FIG. 4) that provides a secondarily actuated slidable electrode member for compressing tissue laterally outward while providing increased electrode engagement area with medial tissue layers.
Figure 9B:
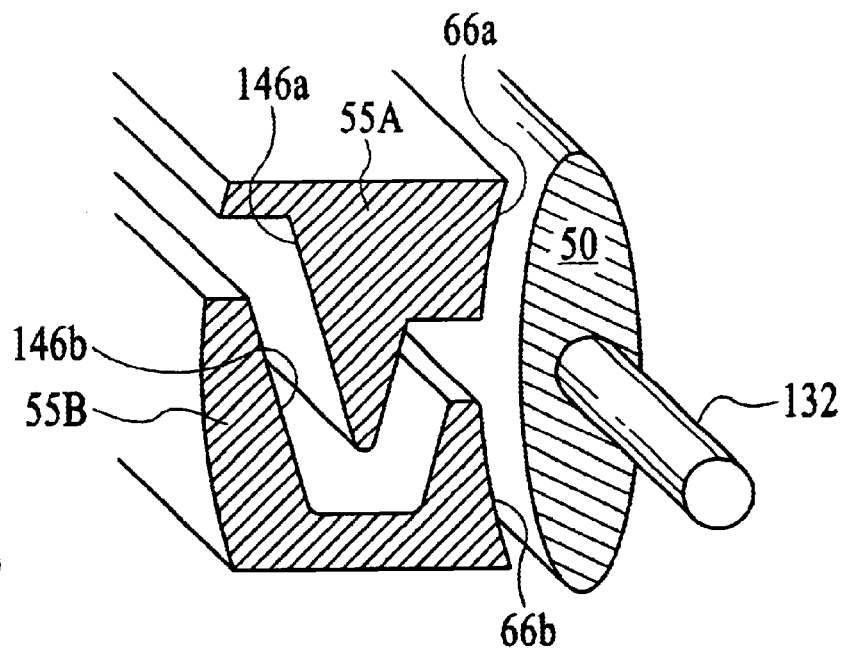
FIG. 9B is an enlarged sectional view of the Type "B" device of FIG. 9A taken along line 9B—9B of FIG. 9A (showing one side of the jaw members in plain view) illustrating an increased area for electrode engagement with medial tissue layers.

2. Typo "B" Working End for Sealing or Welding Tissue. A Type "B" working end 105 is substantially the same as shown in FIGS. 2–3 with the addition of an independently actuatable extension sleeve member 122 that carries core electrode 50 as shown in FIGS. 9A–9B. In the Type "B" system of FIG. 9A, all component parts that are identical to those of the Type "A" embodiment have the same reference numeral. FIG. 9A shows the blade member 30 is coupled to an inner extension member 132 that can be translated from a retracted position to an extended position (see FIG. 9A) to transect captured tissue as described previously. FIG. 9A shows the blade assembly without the jaw structure to illustrate that extension sleeve member 122 is adapted to independently slide over inner extension member 132. By separating the components of the invention that actuate the blade member 30 and the extension sleeve 122 that carries the core electrode 50 as well as tissue-compression means, the level of tissue compression can be better controlled The extension sleeve 122 has a distal taper indicated at 134 with core electrode 50 covering the surface of extension sleeve 122. The extension sleeve 122 is actuatable from a first retracted position to an extended position (see FIG. 9A) by an independent lever or slider mechanism in the handle (not shown) of the instrument. It can be easily understood that the independently actuated extension sleeve 122 is adapted to plow into and compress the transected margin of the engaged tissue outwardly against the cooperating jaw surfaces. Referring to FIG. 9B, an enlarged sectional view of one side of the jaw structure is shown that provides increased electrode engagement surfaces $e_1$ and $e_2$. In this embodiment, the electrode engagement area $e_1$ at the exterior surface s of the vessel is enhanced by cooperating undulations 77 in jaws faces 146a and 146b. Further, the exemplary embodiment of FIG. 9B shows that electrode engagement area $e_2$ is enhanced by providing an oval shape to the core electrode 50 that cooperates with jaw faces 166a and 166b. The embodiment of FIG. 9B also shows that the entire jaw members may comprise electrodes 55A and 55B, which may particularly suitable for very small diameter instruments.

Figure 10:
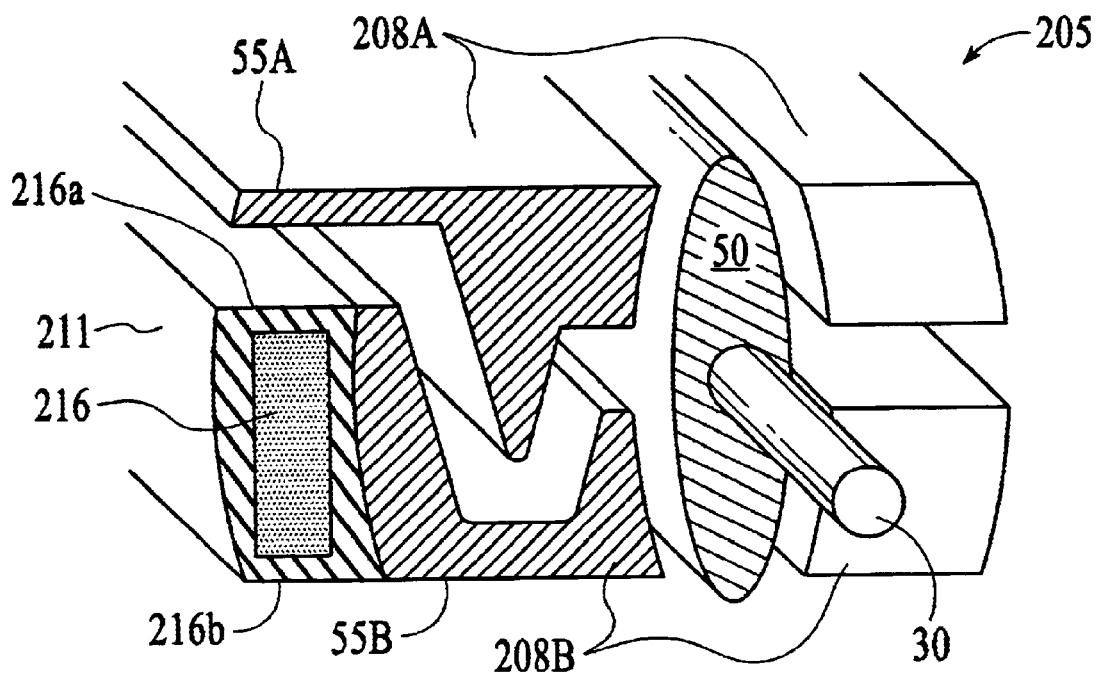
FIG. 10 is a sectional view Type "C" working end of the present invention similar to the working end of FIG. 9A with thermoelectric cooling elements for preventing collateral thermal damage to tissue during the tissue-welding process.

3. Type "C" Working End for Sealing Tissue. FIG. 10 shows an alternative embodiment of a working end 205 and jaw structure that performs the previously described tissue welding methods of the invention. The transecting blade member 30 cooperates with paired jaw members 208A and 208B similar to the previous embodiments. FIG. 10 shows that a novel feature of this embodiment comprises active tissue-cooling means carried within at least one lateral portion 211 of the lower jaw 208B for cooling tissue volumes collateral to the transected margin that is targeted for welding. The tissue-cooling means comprises thermoelectric cooling elements (or Peltier elements) 210 comprising at least one layer of semiconductor blocks (erg., bismuth telluride) within inner and outer heat conduction layers 216a and 216b of a plastic or other material that in not electrically conductive. The use of such semiconductor cooling of tissue engaged by jaw members of a working end (together with thermal energy delivery means) for tissue welding was first disclosed by an author in co-pending U.S. patent application Ser. No. 09/110,065 filed Jul. 3, 1998, which is incorporated herein by this reference. Such semi-conductor cooling elements are coupled to leads wires and a direct current electrical source (not shown) as is known in the art for drawing heat from the engaged tissue and radiating the heat into the environment from the outer surfaces 216a and 216b. The desired parameters for such semiconductor cooling elements can be derived from engineering manuals knows in the art (see, e.g., *Thermoelectric Product Catalog and Technical Reference Manual* published by Ferrotec America Corp., 1050 Perimeter Rd., Manchester, N.H. 03103). FIG. 10 further shows that the jaws of the invention optionally may be asymmetric. That is, the jaws may be designed to seal only one margin of the transected tissue, as would be useful in a lung scion or any other procure in which it is not necessary to seal the margin of tissue that is transected and removed.

Figure 11:
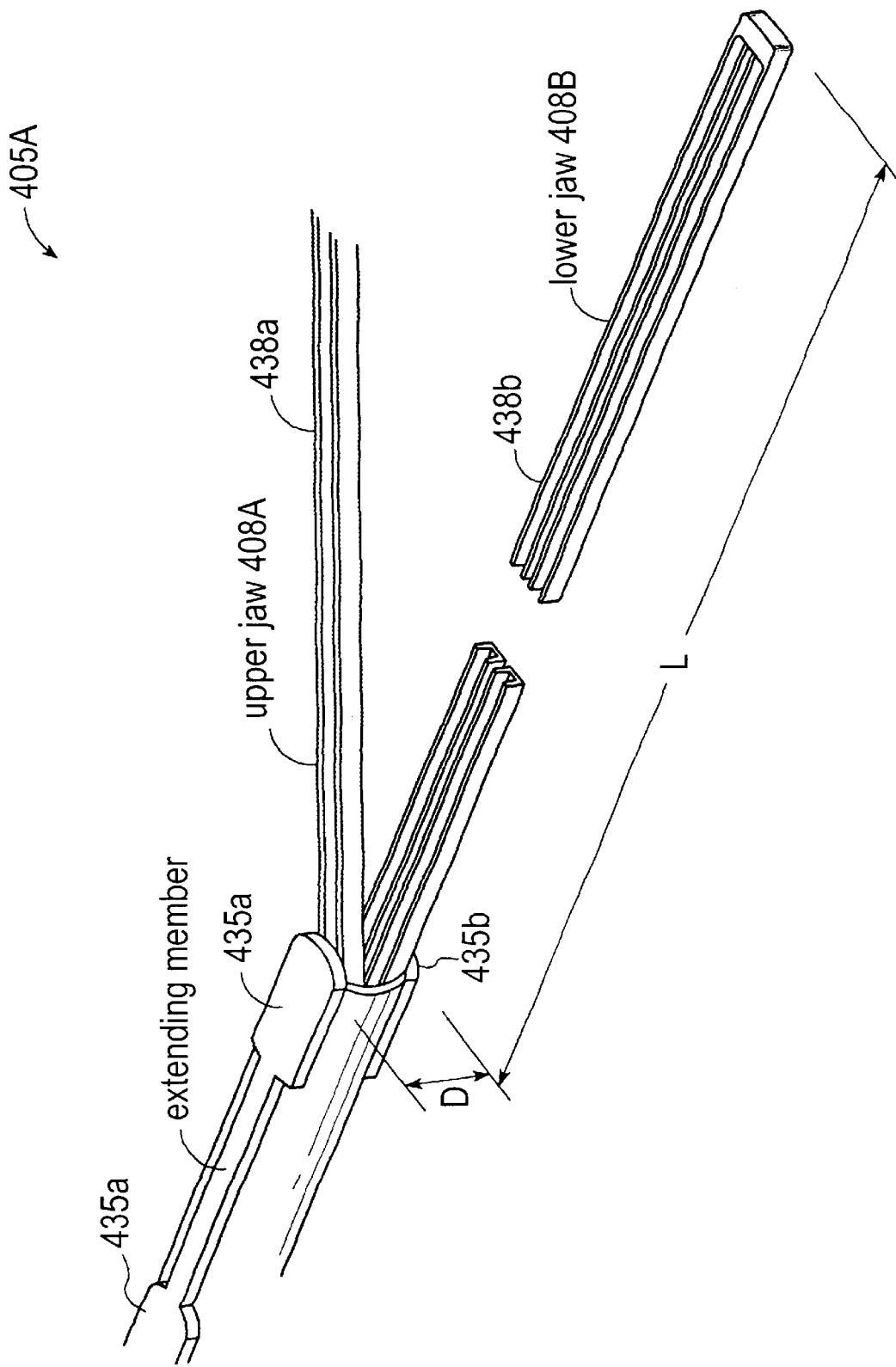
FIG. 11 is a perspective view of a Type "D" working end of the present invention with the cooperating elongate jaw members in a first (open) position and an extending member in a first (retracted) position.

4. Type "D" Working End for Creating High Compression Forces Over Elongate Jaws. FIG. 11 shows an alternative embodiment of working end 405A that carries very elongate jaws similar in shape structure to those illustrated in FIG. 9B. The length L of the jaws may be up to about 20 cm. or more, e.g., for lung resection. The concept of "elongate" jaws having Pension L is to be referenced to the cross-section or diameter D of the introducer that carries the jaw members. The invention describes a system that will allow, for example, 6 to 10 cm long jaws in a 4 to 5 mm. diameter cross-section that can still apply very strong clamping pressure over the entire length of the jaws. It has been found that such high compression is required for effective Rf sealing or welding of captured tissue.

Figure 12:
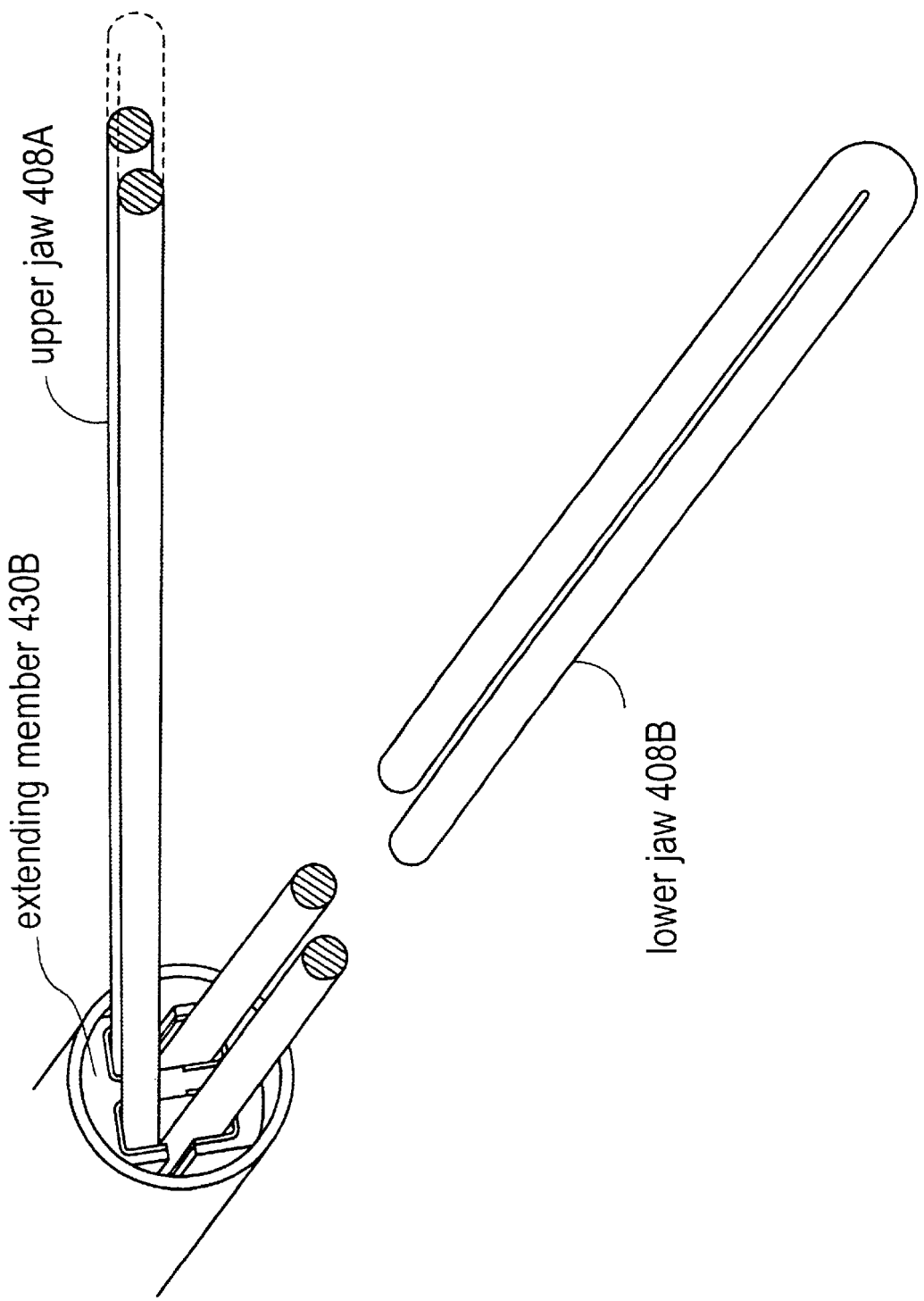
FIG. 12 is a perspective view of another Type "D" working end with jaw members formed of round-stock material for small diameter instruments.

FIG. 12 shows an alternative jaw structure 405B that operates identically to that of FIG. 11, except that the cross-section of each element of the jaws is a simple round shape that is preferred for the fabrication of small diameter working end (eg., 5 mm. diameter or less) whereas the configuration of FIG. 12 is suited for approximately 6–10 mm. instruments.

FIG. 13 depicts the longitudinal view of elongate jaws 408A and 408B with an extending or extension member (after transecting captured tissue) of the type illustrated in FIGS. 3 & 4 above. It can be seen that the flange or cam elements 35a and 35b effectively clamp the distal portion of the jaws closed. However, with substantially elongate jaws relative to their cross section, the medial portion of jaws can tend to flex outwardly thus preventing controlled high compressive forces when clamping tissue indicated at T.

Figure 14:
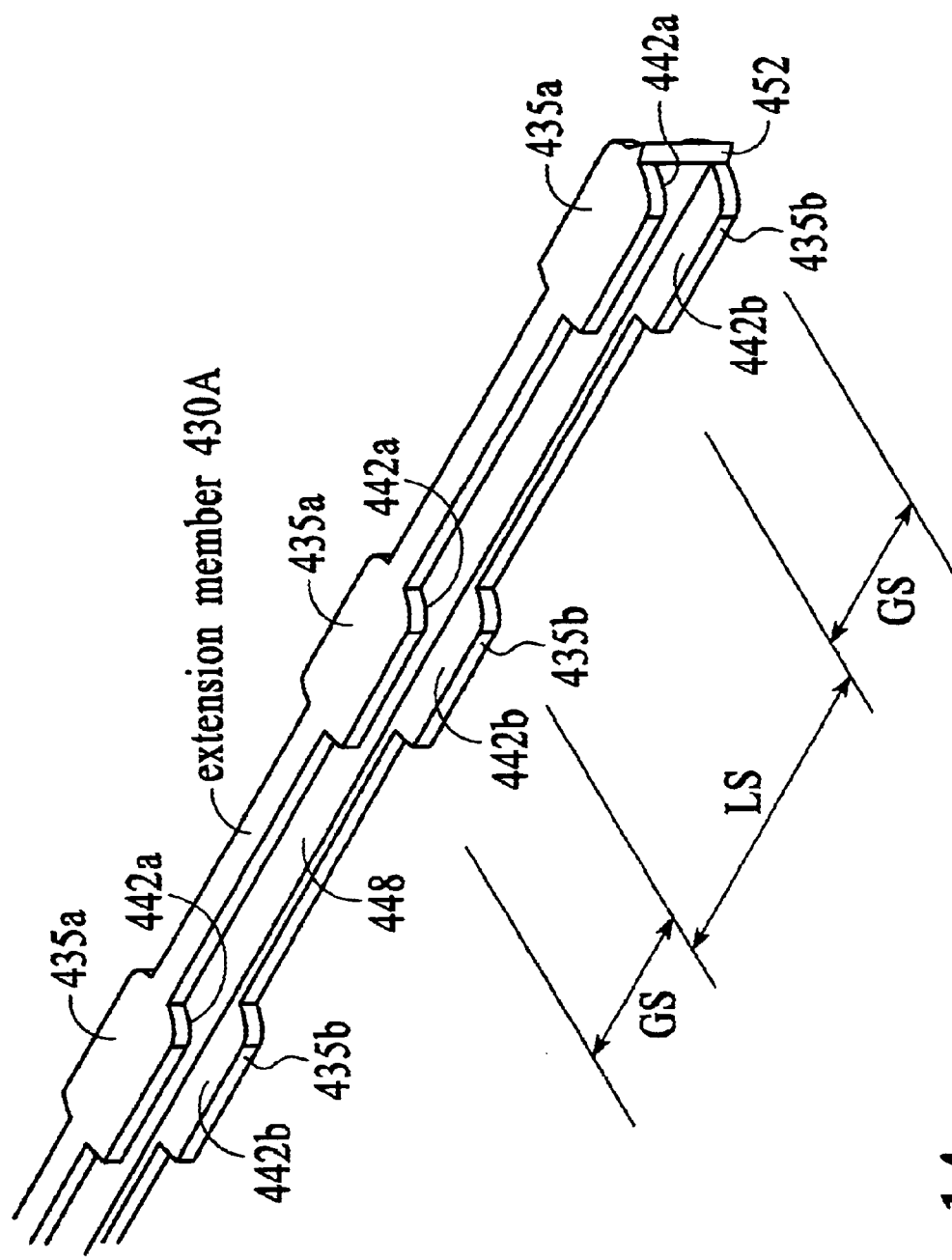
FIG. 14 is a perspective view of the extending member of the Type "D" working end of FIG. 11 illustrating a plurality of flange portions adapted to maintain high compression over elongate jaws.

FIG. 14 depicts the novel longitudinal extending member 430A adapted for closing the jaws of the Type "D" device of FIG. 11 that carries a plurality of cam or flange portions 435a and 435b that provide spaced apart (or continuous) contacts with jaws 408A and 408B (see FIG. 11) to effectively clamp tightly all portions along the length of jaws. As can be seen in FIGS. 14 &, 15, the plurality of flange portions 435a and 435b provide a collective longitudinal cam surface dimension CS for engaging the exterior jaws surfaces that ranges from about 10 percent to 50 per cent of the jaw's longitudinal engagement surface dimension. More preferably, the collective longitudinal cam surface dimension ranges from about 20 percent to 100 per cent of the jaw's longitudinal engagement surface dimension. The central web section 448 of the extending member 430A caries an electrode arrangement as described previously. The distal end of extending member 430A carries a cutting element 452 that can be a blade or an electrode as described previously. If the cutting element is a high voltage cutting electrode, it is insulated apart from the adjacent portions of the extending member and electrodes carries thereon.

Stated in another manner, referring to FIG. 15, the objective of the invention is limit the longitudinal space dimension LS between any of a plurality of surfaces 442a and 442b that engage the cooperating exterior surfaces 438a and 438b of the paired jaws. In this case, the invention provides that the non-engaged or non-cammed spaces define a longitudinal space dimension LS that is less than about 50% of the jaw length. More preferably, the longest non-engaged or non-cammed length LS is less than about 25% of the jaw length L (see FIG. 11).

Figure 16:
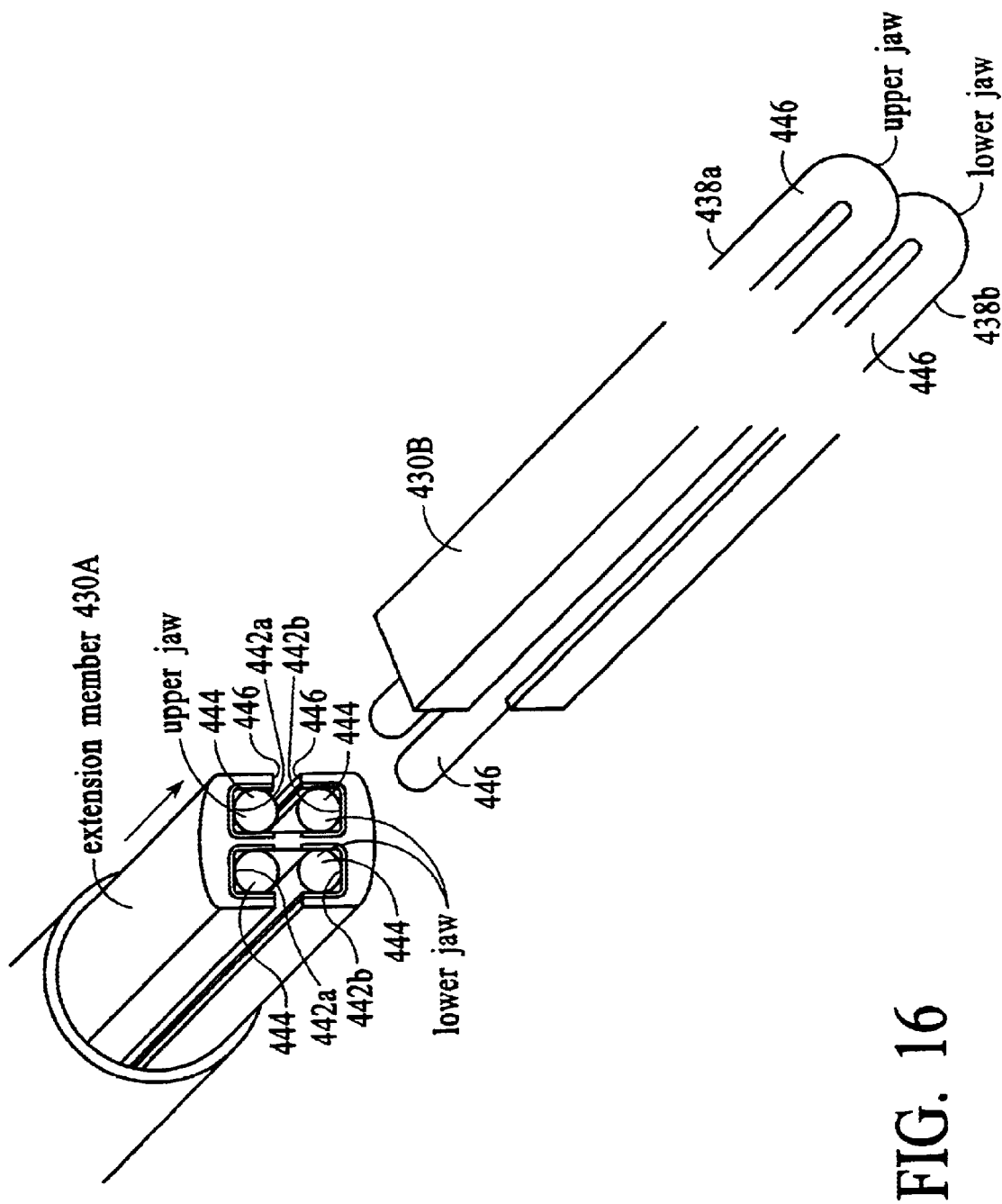
FIG. 16 is a perspective view of an exemplary extending member of the Type "D" working end of FIG. 12 illustrating a continuous camming surface and lateral confining surface that cooperates with exterior jaws faces.

FIG. 16 illustrates an "I"-beam type extending member 430B that is adapted to cooperate with the jaws of FIG. 12 that have a round cross-section. In this embodiment, the cam surfaces 442a and 442b of the extending member 430B are continuous longitudinally for engaging the entire elongate cooperating exterior surfaces 438a and 438b of the paired jaws. Also of particular interest, the engaging or camming surfaces 442a and 442b have outward lateral portions indicated at 444 that at least partially engage the lateral surfaces 446 of the jaws to prevent the jaws from flexing laterally outward when engaging tissue. For substantially small cross-section instruments (e.g., D=5.0 mm. or less), it has been found that continuous camming surfaces 442a and 442b together with lateral engaging surfaces 444 are required to achieve the desired functionality.

5. Type "E" Working End Carrying Multiple Cooperating Electrode Elements.

Figure 17:
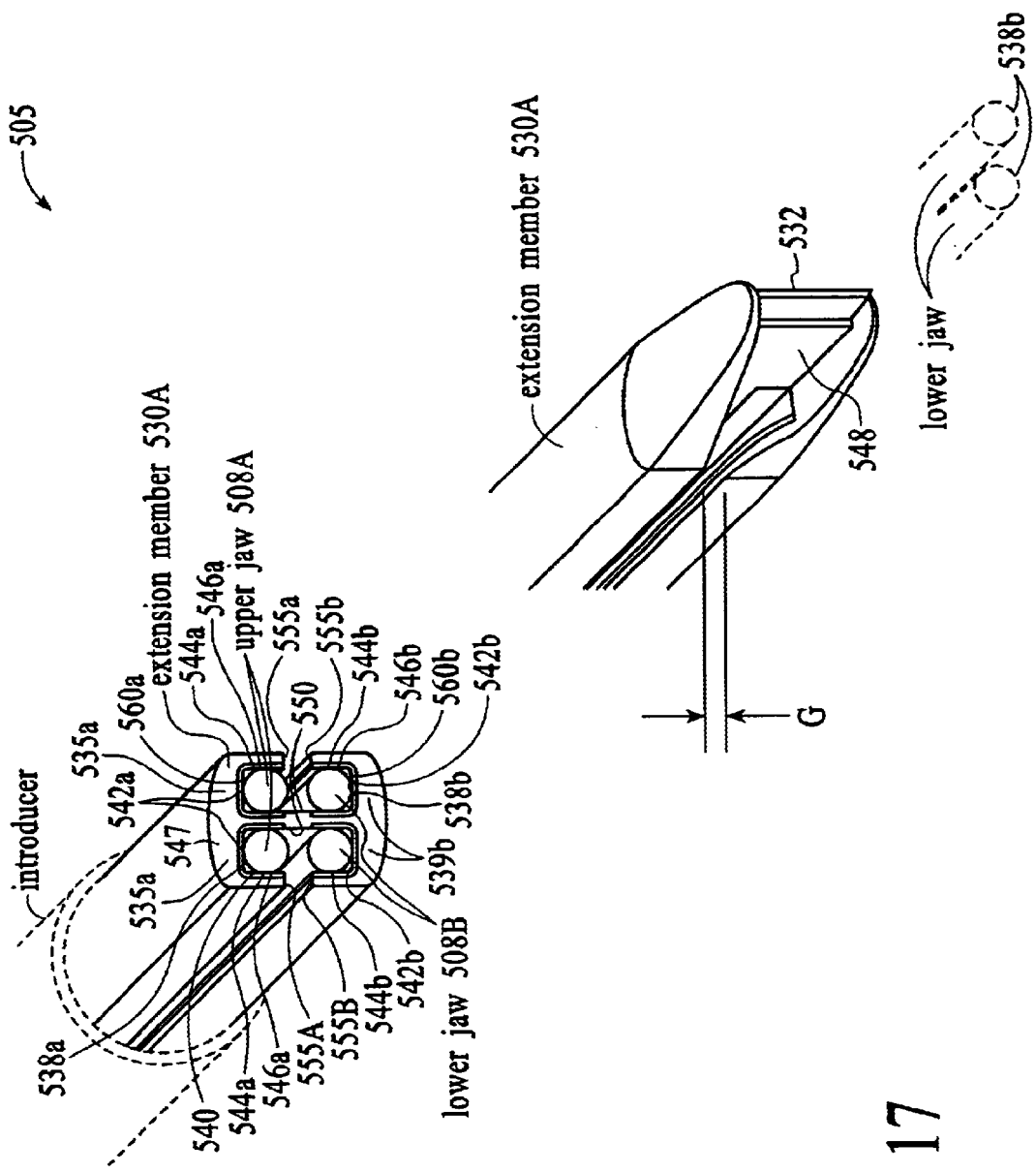
FIG. 17 is a cut-away view of a Type "E" working end with an alternative electrode arrangement.
Figure 18:
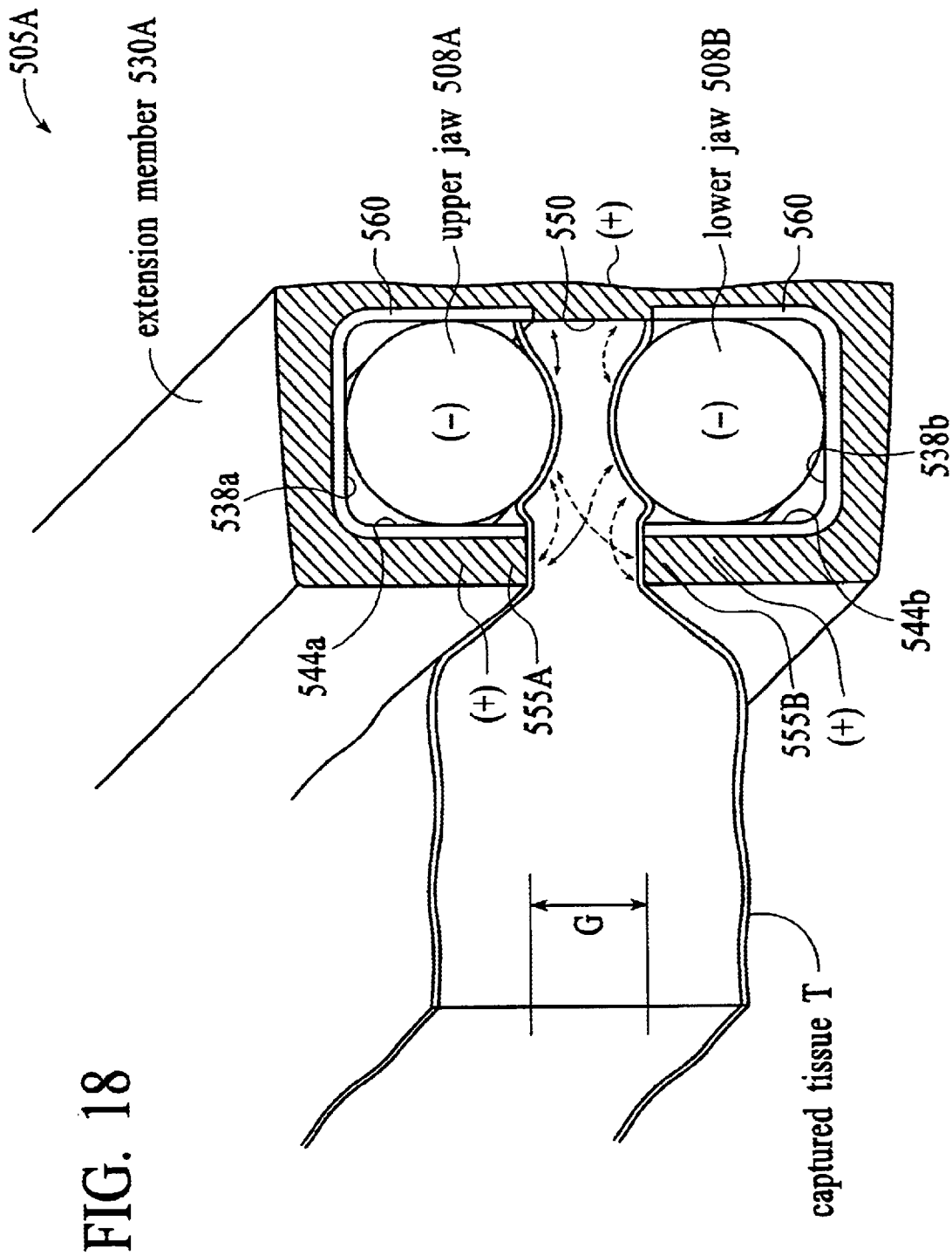
FIG. 18 is a sectional view of the working end of FIG. 17 engaging tissue and illustrates paths of Rf current flow.

FIGS. 17 & 18 illustrate an alternative embodiment of working end 505A that carries very elongate jaws similar in shape structure to those illustrated in FIG. 16. The length of the jaws again may be from 10–20 cm. or more for performing elongate sealing and resection procedures.

FIG. 17 depicts a cut-away view of upper jaw 508A and lower jaw 508B that are formed of round cross-section material for simplicity, as described above with reference to FIG. 12. The extension member 530A again is adapted to actuate the paired jaws from the first open position toward the second closed position as leading edge electrode 532 transects the captured tissue. As can be seen in FIG. 17, the longitudinal extending member 530A has longitudinally continuous cam (flange) portions indicated generally at 535a and 535b that provide continuous longitudinal contact with jaws 508A and 508B (cf. FIG. 16) to effectively cause high compression forces along the entire length of the jaws when in the jaws are in the closed position.

Extension member 530A in FIG. 17 provides channels 540 that define cam surfaces 542a and 542b as the portions of channels 540 that actuate the first and second jaws toward the closed position as these surfaces slidably cooperate with exterior surfaces 538a and 538b of the first and second jaws. The channels 540 of the extending member also defines lateral surfaces 544a and 544b at the outer sides of the member to slidably engage lateral surface portions 546a and 546b of the first and second jaws to prevent the jaws from flexing laterally outward when applying high compression forces to engaged tissue volumes.

FIG. 17 shows the distal end of extension member 530A that cares cutting electrode 532 that is insulated from body material 547 of the extension member with the insulation detail not shown. The distal end of the extension member can be suitably tapered for provide for the cutting electrode 532 to lead through engaged tissue.

Of particular interest, FIG. 17 further shows that central transverse web section 548 of extension member 530A carries exposed electrode surface portions indicated at 550 (collectively) that are adapted to engage medial portions of the transected tissue. Further, additional outboard exposed electrode surface portions indicated at 555a and 555b are provided in member 530A. In this embodiment, the body 547 of extension member 530A is made of a conductive material, such as a metal, thus making exposed electrode surface portions 550 and 555a–555b essentially a common electrode having a polarity indicated as a positive (+) polarity in FIG. 17 & 18 for purposes of illustration. In this embodiment, the upper jaw 508A and lower jaw 508B have the same polarity—which is opposed to the polarity of exposed electrode portions 550 and 555a–555b carried by the extension member. In this case, for purposes of illustration, the jaws 508A and 508B are indicated to have a negative (−) polarity. The electrodes are coupled to electrical source 60 and controller 70 as described above that defines these polarities during operation of the instrument.

As can be seen in FIG. 17, the extension member 530A carries insulator layers 560 (collectively) in the upper and lower channels 540 of the member, respectively. The insulator layers are of Teflon of any other suitable lubricious plastic that can line the sides of channels 540 to insure that the jaw-electrodes cannot contact the exposed electrode portions 550 and 555a–555b that are carried in various upper and lower flange portions and central transverse portion of extension member 530A.

Now turning to FIG. 18, the manner of operating the system and the nature of Rf current flow among the electrodes can be described For convenience, FIG. 18 provides an enlarged view of only one side of jaw assembly 505A and Rf current flow within captured tissue at one margin of the transected tissue T. Of course, the other tissue margin (not shown) could receive a similar form of energy delivery, or alternatively, the other transected margin could not be sealed as would be appropriate for some procedures. FIG. 18 shows a single anatomic structure such as a lung with surface layers and medial tissue captured between the jaws, but it should be appreciated two layers of tissue, lumened structures or tissue bundles can be captured and sealed or welded in a similar manner. As can be seen in FIGS. 17 and 18, the outboard electrode surfaces 555a–555b slidably come into contact with the outward portions of the captured tissue which advantageously provides means for directing Rf current flow to and from these regions. FIG. 17 shows that the leading edge of these outboard electrode surfaces 555a–555b have a tapered distal end to allow them to easily slide over tissue as it is engaged by the jaws. In all of the above instruments, the longitudinal gap G between the inner jaw faces to be any selected dimension that best suited for the thickness of tissue being welded or sealed.

Of particular interest, Rf current paths in the captured tissue flow between the electrode portions of opposing polarities, for example from the upper jaw electrode 508A to both (i) the electrode portion 550 in contact with the transected margins of the medial tissue, and (ii) to electrode portions 555a and 555b in both upper and lower portions of the extension member 530A as depicted by the arrows. Likewise, similar Rf current flows from the lower jaw 508B to electrode portions 550 and 555a–555b. It has been found that such Rf current flow paths from the medial tissue-engaging electrode 550, as well as current flow across the captured tissue, can create an effective weld, particularly when the tissue is maintained under very high compression provided the jaw assembly of the invention.

Figure 19A:
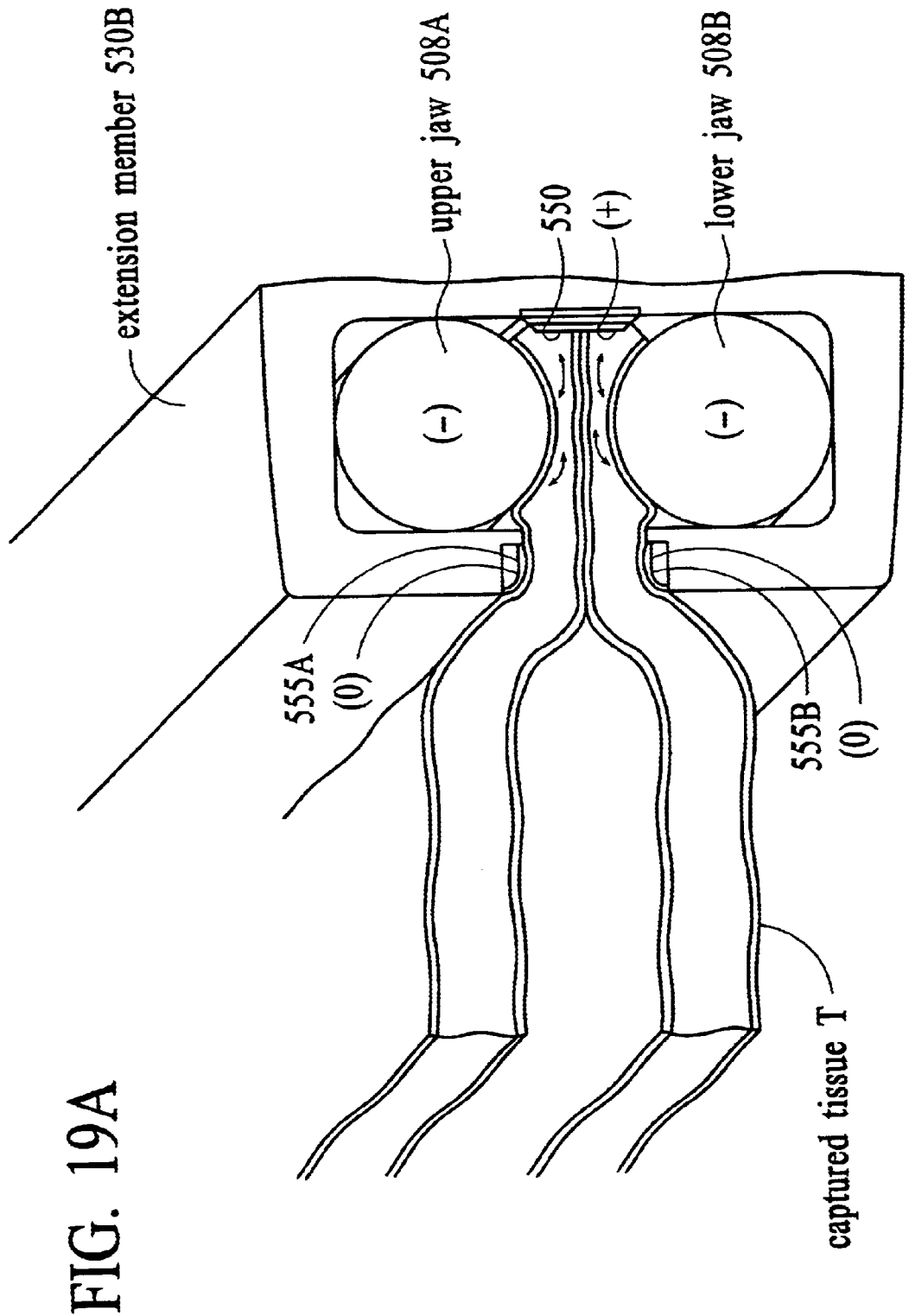
FIGS. 19A–19B are additional sectional views of a Type "E" working end with and alternative electrode arrangement illustrates alternative paths of Rf current flow.
Figure 19B:
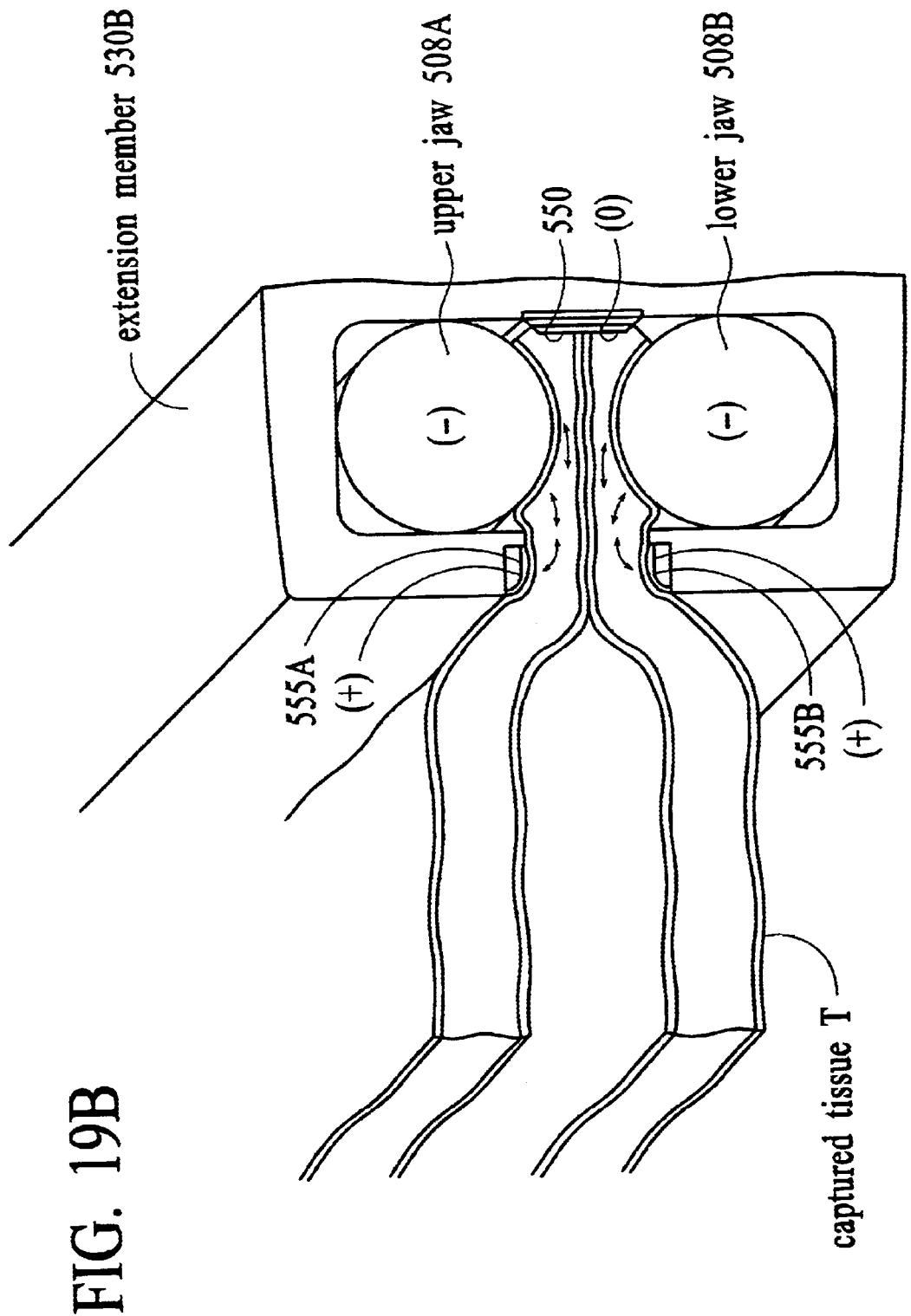

FIGS. 19A–19B show a variant of the "Type E" jaws structure of FIG. 17 that can operate exactly as shown in FIG. 18 or in a multiplexed mode indicated in FIGS. 19A–19B. In this embodiment, the upper and lower jaws 508A and 508B are the same as described above. However, in the embodiment shown in FIG. 19A, extension member 530B can be formed of a non-conductive material (or a conductive material) but carries exposed electrode surface portions 550, 555a and 555b that are independent of one another. One manner of fabricating such electrodes is to make a thin metallic electrode with an insulated backing that can be bonded to the extension member 530B, together with an insulated lead coupled back to the electrical source. In one manner of operation, the controller can maintain electrodes 555a–555b having a common polarity during operation, in which case the Rf current patterns would be the same as depicted in FIG. 18.

In an alternative mode of operation, the controller can automatically sequence Rf current flows between selected pairs of electrodes, since electrode surface portions 550, and 555a and 555b are all independently coupled to the electrical source and controller. In the following description as well as the Figures, the de-activation (or disconnection) of one electrode from the electrical source and controller is indicated by a lack of polarity or a zero (O) when the active polarities are indicated at (+) and (−). For example, FIGS. 19A–19B indicate that for the controller 70 can rapidly de-activate the electrodes 555a and 555b in sequence thereby causing Rf current flow to alter its path from the jaw electrodes 508A and 508B which can prevent rapid tissue desiccation that otherwise might occur in one spot if current flow were in less of a flux, FIG. 19A shows electrode 550 cooperating with the jaw electrodes with the outboard electrodes 555a and 555b being non-active. FIG. 19B shows the outboard electrodes 555a and 555b being active in cooperation with the jaw electrodes with electrode 550 being non-active.

The scope of the invention encompasses multiplexing such Rf current flow among any single pair, or combination of pairs, of electrodes carried by the working end, and still further encompasses making the jaws 508A and 508B with optional independent opposing polarities. Such systems can maintain Rf cent flow in a state of flux to uniformly heat captured tissue without creating hot spots. It has been found that such techniques can contribute to the creation of an effective weld in tissue—when accompanied by high compression provided by the invention. The system preferably uses the sensors and feedback control systems described above in previous embodiments.

Another embodiment of the invention (not shown) may combine linear stapling means with the welding techniques of the invention. In other words, rows of staples together with staple driving means can be carried in elongate jaws portions lateral to the electrodes 55A–55B (see FIG. 7A) carried in the jaws. Such stapling means are known in the art (see, e.g., U.S. Pat. No. 5,403,312 to Yates et al).

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A jaw assembly of a surgical instrument, comprising:
   an instrument working end carrying first and second jaws actuatable between a first open position and a second closed position, the jaws in the closed position defining a longitudinal axis and wherein the jaws further define exterior faces and interior jaw faces having a longitudinal length;
   an axially extending member that is actuatable from a first retracted position to a second extended position in an axial channel extending the length of the exterior and interior jaw faces; and
   wherein said axially extending member defines first cam surface portions that engage cooperating second cam surface portion that extend the entire length of the interior jaw faces to actuate the jaws toward the closed position and prevent flexing apart of said jaws.

2. The jaw assembly of claim 1 further comprising at least one electrode carried in an interior face of at least one of said jaws.

3. The jaw assembly of claim 1 wherein a distal portion of the axially extending member carries a cutting element for transecting tissue.

4. The jaw assembly of claim 3 wherein the cute element is selected from the class consisting of cutting electrodes and cutting blades.

5. The jaw assembly of claim 1 wherein said first cam surface portions of said axially extending member are carried in a plurality of spaced apart flanges.

6. A jaw assembly of a surgical instrument, comprising:
   an instrument working end carrying paired openable and closeable jaws, the opposing jaw faces in the closed position defining a longitudinal axis;
   an extension member that is slidable from a fast retracted position to a second extended position in a longitudinal channel within said paired jaws; and
   said extension member having first surfaces that engage cooperating second surfaces of said paired jaws over the entire length of the jaw faces to move the jaws toward the closed position and maintain the jaws with a selected gap therebetween with the extension member in the second position.

7. The jaw assembly of claim 6 wherein at least one first polarity electrode is carried in an engagement surface of a jaw and at least one second polarity electrode carried in an engagement surface of the extension member.

8. The jaw assembly of claim 7 further comprising an electrical source coupled to said first and second polarity electrodes that define said opposing first and second polarities.

9. A jaw assembly of a surgical instrument, comprising:
   an instrument working end carrying paired openable and closeable jaws, the jaws in the closed position defining a longitudinal axis;
   an extension member that is slidable from a first retracted position to a second extended position in a longitudinal channel within said paired jaws;
   said extension member having first surfaces that engage cooperating second surfaces of said paired jaws over a substantial longitudinal length of the jaws to move the jaws toward the closed position and maintain the jaws with a selected gap therebetween with the extensionsion member in the second position; and
   wherein said first surfaces in the second position extend about laterally-outward second surfaces of said jaws.

10. A jaw assembly of a surgical instrument, comprising:
    an instrument working end carrying paired openable and closeable jaws, the jaws in the closed position defining a longitudinal axis;
    an extension member that is slidable from a first retracted position to a second extended position in a longitudinal channel within said paired jaws;
    said extension member having first surfaces that engage cooperating second surfaces of said paired jaws over a substantial longitudinal length of the jaws to move the jaws toward the closed position and maintain the jaws with a selected gap therebetween with the extensionsion member in the second position; and
    wherein a portion of said first surfaces comprises a conductor defining a first polarity and spaced apart portions of said extension member carry a conductor defining a second polarity.

11. A jaw assembly of a surgical instrument, comprising:
    an instrument working end carrying paired openable and closeable jaws, the jaws in the closed position defining a longitudinal axis;
    an extension member that is slidable from a first retracted position to a second extended position in a longitudinal channel within said paired jaws;
    said extension member having first surfaces that engage cooperating second surfaces of said paired jaws over a substantial longitudinal length of the jaws to move the jaws toward the closed position and maintain the jaws with a selected gap therebetween with the extensionsion member in the second position; and
    wherein inward portions of said first surfaces comprises a conductor defining a first polarity and laterally outward portions of said extension member carry a conductor defining a second polarity.

* * * * *